United States Patent [19]

Itakura et al.

[11] Patent Number: 5,583,013

[45] Date of Patent: *Dec. 10, 1996

[54] METHOD AND MEANS FOR MICROBIAL POLYPEPTIDE EXPRESSION

[75] Inventors: Keiichi Itakura, Arcadia; Arthur D. Riggs, La Verne, both of Calif.

[73] Assignee: Genentech, Inc., South San Francisco, Calif.

[*] Notice: The term of this patent shall not extend beyond the expiration date of Pat. No. 4,366,246.

[21] Appl. No.: 434,321

[22] Filed: May 2, 1995

Related U.S. Application Data

[63] Continuation of Ser. No. 79,994, Jun. 18, 1993, abandoned, which is a continuation of Ser. No. 821,711, Jan. 15, 1992, Pat. No. 5,221,619, which is a continuation of Ser. No. 726,631, Jul. 1, 1991, abandoned, which is a continuation of Ser. No. 593,488, Oct. 9, 1990, abandoned, which is a continuation of Ser. No. 317,132, Feb. 28, 1989, abandoned, which is a continuation of Ser. No. 839,855, Mar. 14, 1986, abandoned, which is a continuation of Ser. No. 90,979, Nov. 5, 1979, Pat. No. 4,704,362, which is a continuation-in-part of Ser. No. 849,692, Nov. 8, 1977, Pat. No. 4,785,420.

[51] Int. Cl.$^6$ .............................. C12P 21/02; C12N 15/70
[52] U.S. Cl. ................... 435/69.4; 435/69.1; 435/320.1; 435/172.3; 435/252.3; 435/252.33; 536/23.51; 935/60; 935/72; 935/73; 935/13; 935/29
[58] Field of Search ............................ 435/69.1, 320.1, 435/252.3, 252.33, 91.1, 69.8, 69.7, 69.6, 69.3, 69.5, 69.52, 91.4; 536/23.1, 23.2, 23.4, 24.2, 24.1, 22.5; 935/2, 6, 9, 10, 11, 13, 23, 29, 38, 40, 41, 60, 66, 72, 73

[56] References Cited

U.S. PATENT DOCUMENTS

| | | |
|---|---|---|
| 4,082,613 | 4/1978 | Thirulmalachar et al. ............. 435/69.4 |
| 4,190,495 | 2/1980 | Curtiss, III ..................... 435/172.3 |
| 4,237,224 | 12/1980 | Cohen ......................... 435/69.1 |
| 4,264,731 | 4/1981 | Shine ......................... 435/91.41 |
| 4,321,365 | 3/1982 | Wu et al. ..................... 536/24.2 |
| 4,332,892 | 6/1982 | Ptashne et al. ................. 435/69.7 |
| 4,363,877 | 12/1982 | Goodman et al. ................ 435/320.1 |
| 4,366,246 | 12/1982 | Riggs ......................... 435/69.8 |
| 4,407,948 | 12/1983 | Goodman et al. ................ 435/91.52 |
| 4,440,859 | 4/1984 | Rutter et al. ................. 435/91.41 |
| 4,468,464 | 8/1984 | Cohen et al. .................. 435/320.1 |
| 4,704,362 | 11/1987 | Itakura et al. ................ 435/252.3 |
| 5,221,619 | 6/1993 | Itakura et al. ................ 435/69.4 |

FOREIGN PATENT DOCUMENTS

| | | |
|---|---|---|
| 78 08050 | 3/1977 | France . |
| 1521032 | 8/1978 | United Kingdom . |

OTHER PUBLICATIONS

Anonymous, Purported contents of presentation by Walter Gilbert at 16th Insulin Symposium (1976).
Backmam, *Molecular Cloning of the Lambda Repressor Gene (cI)*, Harvard Univ. Thesis (1977).
Baltimore, *Recombinant Molecules: Impact on Science and Society*. New York: Raven Press, 1977, pp. 337–352.
Berg et al., *Summary Statement of the Asilomar Conference on Recombinant DNA Molecules*, 72(6):1981–1984 (1975).
Brown et al., *Molecular Mechanisms in the Control of Gene Expression*. New York: Academic Press, Inc., 1976, pp. 487–493.
Cameron et al., *Science*, 196:212–214 (1977).
Carbon et al., *Recombinant Molecules: Impact on Science and Society*. New York: Raven Press, 1977, pp. 355–378.
Clarke et al., *Proc. Nat. Acad. Sci.*, 77(11):4361–4365 (1975).
Cohen, "DNA Cloning in the Study of Prokaryotic and Eukaryotic Biology" *Proc. Miami Wint. Symposium*, pp. 1–56, 1977.
Curtiss, *Am. Rev. Microbiol.*, 30:507–533 (1976).
Eli Lilly and Company (Summary, 16th Insulin Symposium).
Glover, *Biochem. of Cell Differentiation II*, 15:1–44 (1977).
Goff et al., *Recombinant Molecules: Impact on Science and Society*, New York: Raven Press, 1977, pp. 285–298.
Gubbins et al., *Gene*, 1:185–207 (1977).
Hamer, *Recombinant Molecules: Impact on Science and Society*, New York: Raven Press, 1977, pp. 317–335.
Hershfield et al., *Proc. Nat. Acad. Sci.*, 71(9):3455–3459 (1974).
Li et al., *Proc. Nat. Acad. Sci.*, 70(4):1112–1116 (1973).
Miller et al., *Biochem*, 16(6):1031–1038 (1977).
Morrison et al., *Journal of Mol. Biol.*, 50:359–371 (1970).
Muller–Hill et al., *Nature*, 249:561–563 (1974).
Murray, *Recombinant Molecules: Impact on Science and Society*, New York: Raven Press, 1977, pp. 249–260.
Murray et al., *Nature*, 251:473–481 (1974).
Newmark, *Nature*, 260:747–748 (1976).
Schimke, "Organization and Expression of Chromoxomes", *Report on Dahlem Workshop*(1976).

(List continued on next page.)

*Primary Examiner*—Christopher S. F. Low

[57] ABSTRACT

The Specification discloses:

1. Recombinant microbial cloning vehicles comprising heterologous DNA coding for the expression of mammalian hormone (e.g., somatostatin) and other polypeptides, including plasmids suited for the transformation of bacterial hosts. The latter incorporate a regulon homologous to the host in its untransformed state, in reading phase with the structural gene for the heterologous DNA;

2. Cloning vehicles coding for the microbial expression of a protein variously comprising (a) a polypeptide hapten and additional protein sufficient in size to confer immunogenicity on the product of expression, which may find use in raising antibodies to the hapten for assay use or in the manufacture of vaccines; and (b) a desired polypeptide product and additional protein from which the desired product may be cleaved; and 3. Methods of preparing synthetic structural genes coding for the expression of mammalian polypeptides in microbial cloning systems.

2 Claims, 10 Drawing Sheets

OTHER PUBLICATIONS

Thomas, *Proc. Nat. Acad. Sci.*, 74(11):4579–4583 (1974).
Tiollais et al., *Gene*, 1:49–63 (1976).
Bernardi, *Nature*, 259:173–174 (1976).
Chang et al., *Cell*, 6:231–(1975).
Falkow, *Recombinant Molecules: Impact on Science and Society*, New York: Raven Press, 1977, pp. 167–175.
Gelfand, NATO Advanced Study Institute: *The Biology of Bacterial Plasmids*, (1976).
Helinski et al., *Recombinant Molecules: Impact on Science and Society*, New York: Raven Press, 1977, pp. 151–165.
Lederberg, "The Least Hazardous Course: Recombinant DNA Technology . . . ", *Recombinant Molecules: Impact on Science and Society*, New York: Raven Press, 1977, pp. 485–494.
Lewin, "Perspectives and Trends in Gene Expression", *Molecular Mechanisms in the Control of Gene Expression*, Academia Press, vol. V, pp. 623–642 (1976).
Murray et al., "Restriction Enzymes and the Cloning of Eukaryotic DNA", *Proceedings of the Tenth FEBS Meeting*, 38:193–207 (1975).
O'Farrell et al., *Journal of Bacteriology*, 134(2):645–654 (1978).
Panasenko et al., *Science*, 196:188–189 (1977).
Polisky, *Grant Award*, Jul. 1, 1977–Jun. 30, 1980.
Rambach et al., *Proc. Nat. Acad. Sci.*, 74(11):5041–5045 (1977).
Riedel et al., "Cloning NIF Genes", *Proc. Miami Winter Symposium*, pp. 115–132 (1977).
Rutter, *Grant Application*, Sep. 1, 1977–Aug. 31, 1980.
Saunders, *Nature*, 262:536 (1976).
Thomas, *Recombinant Molecules: Impact on Science and Society*, New York: Raven Press, 1977, p. 353.
Aviv et al., *Proc. Nat. Acad. Sci.*, 69(6):1408–1412 (1972).
Baxter et al., *Clinical Research*, 25(3):461A (1977).
Biessmann et al., *Biochemistry*, 15(20):4356–4363 (1976).
Both et al., *Proc. Nat. Acad. Sci.*, 72(3):1189–1193 (1975).
Gilmour et al., *J. Cell Physiol.*, 85:449–458 (1975).
Greenblatt et al., *Journal of Mol. Biol.*, 108:361–379 (1976).
Rozenblatt et al., *Proc. Nat. Acad. Sci.*, 73(8):2747–2751 (1976).
Stallcup et al., *Biochemical and Biophysical Research Communications*, 58(1) (1974).
Apte et al., *Nature*, 257:329–331 (1975).
Bukhari et al., *Nature New Biology*, 243:238–241 (1973).
Bukhari, "Degradation of Protein Fragments in *E. coli*", *Intracellular Protein Turnover*, New York: Academic Press, Inc., 1975, pp. 3–16.
Dmitriev et al., *Molec. Gen. Genet.*, 145:317–326 (1976).
Goldberg, *Nature New Biology*, 234:51–52 (1971).
Goldberg, *Proc. Nat. Acad. Sci.*, 69(2):422–426 (1972).
Goldberg, *Proc. Nat. Acad. Sci.*, 69(9):2640–2644 (1972).
Goldberg et al., "Intracellular Protein Degradation", *Annual Review of Biochem.* vol. 43, Annual Reviews Inc. Palo Alto, California pp. 835–869 (1974).
Goldberg et al., *Annual Review of Biochemistry*, pp. 747–803 (1976).
Goldberg et al., *Proteolysis and Physiological Regulation*, pp. 313–337 (1976).
Goldschmidt, *Nature*, 228:1151–1154 (1970).
Hewitt et al., *European Journal of Biochem.*, 74:285–292 (1977).
Kemshead et al., *European Journal of Biochem.*, 71:185–192 (1976).
Kemshead et al., *European Journal of Biochem.*, 45:535–540 (1974).
Lin et al., *The Journal of Biological Chemistry*, 247(7):2205–2211 (1972).
Miller, *Annual Review of Microbiology*, vol. 29 pp. 486–504 (1975).
Miller et al., *Journal of Bacteriology*, 130(1):347–353 (1977).
Pine, *Journal of Bacteriology*, 93(5):1527–1533 (1967).
Platt et al., *Nature*, 228:1154–1156.
Prouty et al., *The Journal of Biological Chemistry*, 250(3):1112–1122 (1975).
Prouty et al., *The Journal of Biological Chemistry*, 247(10):3341–3352 (1972).
Schimke, "Regulation of Protein Degradation in Mammalian Tissues", *Mammalian Protein Metabolism*. New York: Academic Press, Inc., 1970, pp. 177–228.
Vaughan et al., "The Specificity of Protein Biosynthesis", *Advances in Protein Chemistry*. New York: Academic Press, Inc., 1959, pp. 115–173.
Zipser et al., *Journal of Bacteriology*, 127(3):1538–1542 (1976).
Prouty et al., *Nature New Biology*, 240:147–150 (1972).
Rabinovitz et al., *Journal of Bacteriology*, 99(1):336–338 (1969).
Schachtele et al., *Journal of Mol. Biol.*, 33:861–872 (1968).
Shively, "Inclusion Bodies of Prokaryotes", *Annual Review of Microbiology*, Palo Alto: Annual Reviews Inc., (28), 1974, pp. 167–187.
Busse et al., *Carbonylbis (Methionyl) Insulin. A Proinsulin Analogue*, 15(8):1649–57 (1976).
Johansen et al., *Comptes Rendus Des Travaus Du Laboratoire Carlbsburg*, vol. 36, No. 20, Danish Press Ltd., Copenhagen, pp. 365–384 (1968).
Kostyo et al., *Metabolism*, 25(1):105–124 (1976).
Lewis et al., *Endo*, 101(5):1587–1603 (1977).
Singh et al., *Endo*, 94(3):883–891 (1974).
Adams et al., *Nature*, 223:1009–1014 (1969).
Baralle, *Nature*, 267:279–281 (1977).
Cheng et al., *Journal of Mol. Biol.*, 107:527–547 (1976).
Klämbt et al., *Journal of Theor. Biol.*, 58:319–324 (1976).
Lodish, *Journal of Mol. Biol.*, 50:689–702 (1970).
Shine et al., *Nature*, 254:34–38 (1975).
Steege, *Proc. Nat. Acad. Sci.*, 74(10):4163–4267 (1977).
Steitz et al., *Proc. Nat. Acad. Sci.*, 72(12):4734–4738 (1975).
Steitz, *Nature*, 224:957–964 (1969).
Steitz, *RNA Phages*. USA: Cold Spring Harbor Laboratory, 1975, pp. 319–352.
*Technology Review*, 12–13 (1976).
Harvey et al., *Nucleic Acid Research*, 2(11):2007–2020 (1975).
Itakura et al., *The Journal of Biological Chemistry*, 250(12):4592–4600 (1975).
Itakura et al., *Journal of the American Chemical Society*, 97(25):7327–7332 (1975).
Katsoyannis et al., *Biochemistry*, 6(9):2642–2655 (1967).
Khorana, "Synthesis in the Study of Nucleic Acids", *Seventh International Congree of Biochem*, Tokyo Japan (1967).
Koster, *A Total Synthesis of a Structural Gene for the Human Peptide Angiotensin II* :202–220.
Krieger et al., *Proc. Nat. Acad. Sci.*, 73(9):3160–3164 (1976).
Maugh II, *Research News*, 1235 (1971).

Narang et al., *Canadian Journal of Biochemistry*, 55(11):1125–1133 (1977).
Narang et al., *Canadian Journal of Biochemistry*, 53:392–394 (1975).
Narang et al., *Journal of the American Chemical Society*, 96(22):7074–7078 (1974).
Narang et al., *Chemical Synthesis of Dioxyribododicanucleotides*, 8(8): 3443–3451 (1969).
Szekely, *Nature*, 263:277–278 (1976).
Contreras et al., *FEBS Letters*, 24(3):339–342 (1972).
Min Jou, *Nature*, 237:82–88 (1972).
Weigert et al., *Cold Spring Harbor Symposium on Quantative Biology*, pp. 145–150 (1966).
Steiner et al., *Federation Proceedings*, 33(10):2105–2115 (1974).
Lodish, *Annual Review of Biochemisrty*. Palo Alto: Annual Reviews Inc., 45, 1976, 39–72.
Majors, *Proc. Nat. Acad. Sci.*, 72(11):4394–4398 (1975).
Cheng et al., *Gene*, 214:121–130 (1981).
Danilevskaya, *Expression of Eukaryotic Genes in Cells of Escherichia coli*, translated from Genetika, 15(12): 2087–2107 (1979). UDC 575.11:576.851.48 1397–1412.
Glover et al., *Companion to Biochemistry*. pp. 49–78 (1978).
Miller, *Cell Substrates*, New York: Plenum Press. (1978) pp. 153–174.
Nichols et al., *Proc. Nat. Acad. Sci.*, 76(10):5244–5248 (1979).
Simon et al., *Proc. Nat. Acad. Sci.*, 80:2059–2062 (1983).
Article—"Human Gene in *E. Coli*" (Nov. 7, 1977).
Article—"Diabetes Researchers Come Through" *Los Angeles Times* (Sep. 8, 1978).
Alexander, "Scientitsts Describe Bacterial 'Factory'" *Los Angeles Times* (Dec. 2, 1977).
Backman et al., *Proc. Nat. Acad. Sci.*, 73(11):4174–4178 (1976).
Bahl et al., *Gene*, 1:81–92 (1976).
Casadaban et al., *J. Mol. Biol.*, 104:541–555.
Chain, *Biotechnological Application of Proteins and Enzymes*. Academic Press., 1977, pp. 15–17.
Crea et al., *Proc. Nat. Acad. Sci. USA*, 75(12):5765–5769.
Goeddel et al., *Nature*, 281:514–518 (1979).
Goeddel et al., *Proc. Nat. Acad. Sci. USA*, 76(1):106–110.
Guarente et al., *Science*, 209:1428–1430 (1980).
Heyneker et al., *Nature*, 263:748–752 (1976).
Higuchi et al., *Proc. Natl. Acad. Sci USA*, 73(9):3146–3150 (1976).
Humphries et al., *Nucleic Acids Research*, 4:2389–2406 (1977).
Itakura et al., *26th international Congress of Pure and Applied Chemistry*, Tokyo, Japan, Sep. 4–10, 1977, p. 337.
Jackson et al., *Proc. Nat. Acad. Sci. USA*, 69(10):2904–2909.
Khorana et al., *J. Biol. Chem.*, 251( ):565–570.
King et al., *Dictionary of Genetics*, 3rd Ed., Oxford University Press, 1985, p. 334.
Koster et al., *Hoppe-Seyler's Z. Physiol. Chem*, 356(S):1585–1593 (1975).
Kourilsky et al., *Nature*, 267:637–639 (1977).
Laycock et al, *Nature*, 221:1118–1122 (1969).
Liu et al., *Science*, 196:192–195 (1977).
Marians et al., *Nature*, 263(5580):744–748 (1976).
McReynolds et al., *J. Biol. Chem.*, 252(6):1840–1843.
Meagher et al., *Cell*, 10:521–536 (1977).
Mertz et al., *Proc. Nat. Acad. Sci. USA*, 69(11):3370–3374 (1972).

Morrow et al., *Proc. Nat. Acad. Sci. USA*, 71(5):1743–1747 (1974).
Morrow et al., *Proc. Nat. Acad. Sci. USA*, 69(11) 3365–3369.
"Genetic Engineering Will Fight Disease" *San Francisco Chronicle*, Apr. 15, 1976.
Polisky et al., *Proc. Natl. Acad. Sci. USA*, 73(11):3900–3904 (1976).
Rabbitts, *Nature*, 260:221–225 (1976).
Ratzkin et al., *Proc. Natl. Acad. Sci USA*, 74(2):487–491 (1977).
Rougeon et al., *Nucleic Acids Research*, 2(12):2365–2378.
Sanger et al, *Nature*, 265:687–695 (1977).
Scheller et al., *Science*, 196:177 (1977).
Selker et al., *J. Bacteriology*, 129:388 (1977).
Singer et al., *Science*, 181:1114 (1973).
Sinsheimer, *Ann. Rev. Biochem.*, 46:416–38 (1977).
Stenesh, *Dictionary of Biochemistry*, John Wiley & Sons, New York (1975) p. 269.
Struhl et al., *Proceedings of the ICN–UCLA Sumposia V.*, Academic Press, New York (1976) pp. 495–506.
Struhl et al., *Proc. Natl. Acad. Sci. USA*, 73(5):1471–1475 (1976).
Tait et al., *Proceedings fo the ICN–UCLA Symposia V.*, Academic Press, New York (1976) pp. 507–512.
*Transcript of Proceedings*, (Berg, Handler) (1977) pp. 120–121.
Ullrich et al., *International Congress Series*, 468:20–26 (1978).
Ullrich et al., *Science*, 196:1313–1319.
Vapnek et al., *Proc. Natl. Acad. Sci. USA*, 74(8):3508–3512 (1977).
Vosberg et al., *Hum. Genet.*, 40:1–72 (1977).
Williamson, *Nature*, 270:295–297.
Wilson et al., *Science*, 196:200–202 (1977).
Anonymous, "The Artificial Gene", *Technology Review*, Dec. 1976.
Anonymous, "Big Advance In Artificial Gene Studies", *Chronicle*, Aug. 28, 1976.
Air et al., *J. Mol. Biol.*, 107:445–458 (1976).
Air et al., *J. Mol. Biol.*, 96:703–719 (1975).
Fiers et al., *Nature*, 260:500–507 (1976).
Renserger, "Team at M.I.T. Constructs A Fully Functioning Gene", Aug. 29, 1976.
Rensberger, "Synthesis of Working Gene Hailed as a Major Advance", New York Times, Aug. 24, 1976.
Gross et al., *J. Amer. Chem. Soc.*, 83:1510–1511 (1961).
Hancock et al., *Journal of the American Chemical Society*, 97(26):7488–7489 (1975).
Stark, *Methods in Enzymology*, :129–132 (1977).
Dayhoff, *Atlas of Protein Sequence and Structure*, National Biomedical Research Foundation, 5:(2):26–27 (1976).
Dayhoff, *Atlas of Protein Sequence and Structure*, National Biomedical Research Foundation, 5(3):33–35, 46 (1978).
Bornstein et al., *Phosphatridylchotine Requirement for Hemoprotein P–450*, 245(18):4854–4856 (1970).
NIH Guidelines, Federal Register, 14(131):27902–27943 (Jul. 7, 1976).
Itakura et al., *Science*, 198:1056–1063 (Dec. 7, 1977).
Li et al., *PNAS*, 73(5)1476–1479 (1976).
Kimmel et al., *J. Biol. Chem.*, 250(24):9369–9376 (1975).
Yamasaki et al., *J. Biol. Chem.*, 250(7):2510–2514 (1975).
Liu et al., *J. Biol. Chem.*, 247(13):4365–4381 (1972).
Liu et al., *J. Biol. Chem.*, 247(13):4351–4364 (1972).
Gross, E., *Methods Enzymol.*, 11:238–263 (1967).

Mercereau–Puijalon et al., *Nature*, 275:505–510 (1978).
Villa–Komaroff et al., *PNAS*, 75(8):3727–3731 (1978).
Atkins, J., *Nature*, 262:256–257 (1976).
Lehninger, *Biochemistry*, 2nd Edition, pp. 879–881, 961–962, Worth Publishing.
*Chemical and Engineering News*, 55(22):4 (May 7, 1977).
Hall, "Invisible Frontiers" pp. 106–108, 120–121, 149–165, 174–175 (1987) The Atlanta Monthly Press, New York.
Drapeau et al., *J. Biol. Chem.*, 247:6720–6726 (1972).
Gerwin et al., *J. Biol. Chem.*, 241:3331–3339 (1966).
Gilles et al., *FEBS Letters*, 65(3):369–372 (1976).
Koida et al., *J. Biol. Chem.*, 251(23):7593–7599 (1976).
Walter, R., *Biochimica et Biophysica Acta*, 422:138–158 (1976).
Marston, *Biochem. J.*, 240:1–12 (1986).
Guarante et al., *Cell*, 20:543–553 (1980).
Hamlyn et al., *J. Mol. Biol.*, 94:101–109 (1975).
Singleton et al., *Dictionary of Microbiology and Molecular Biology*, Second Edition, Wiley–Interscience (John Wiley & Sons), p. 747 (1987).
Stryer, L., *Biochemistry*, W. H. Freeman and Co., San Fransisco, pp. 816–817 (1975).
Maugh II, *Science*, 188:920–923 (1975).

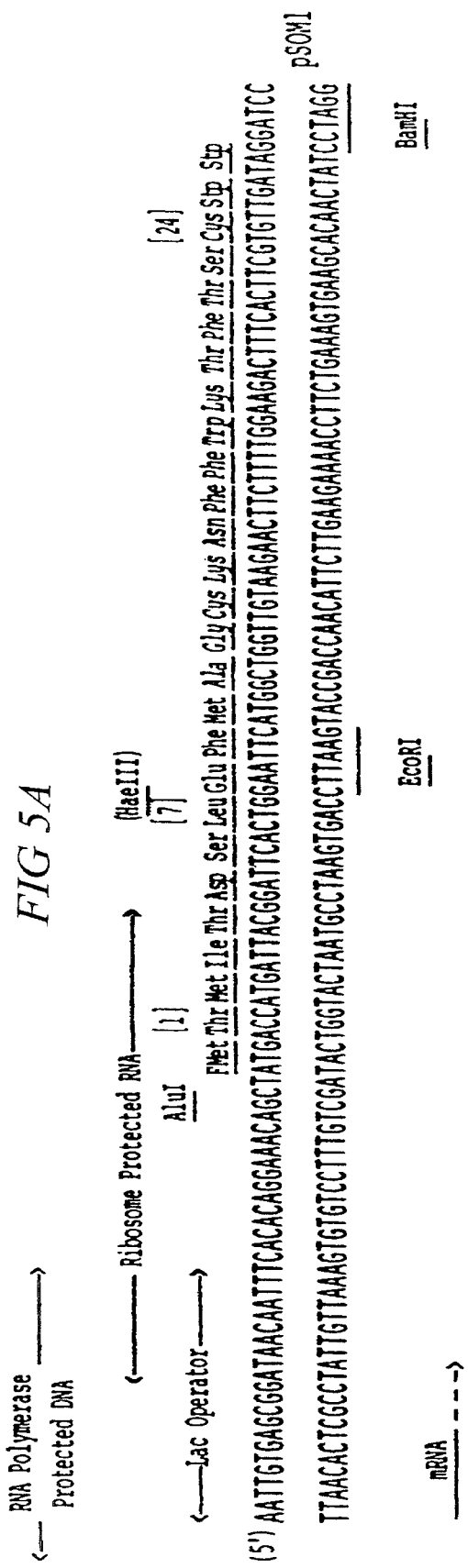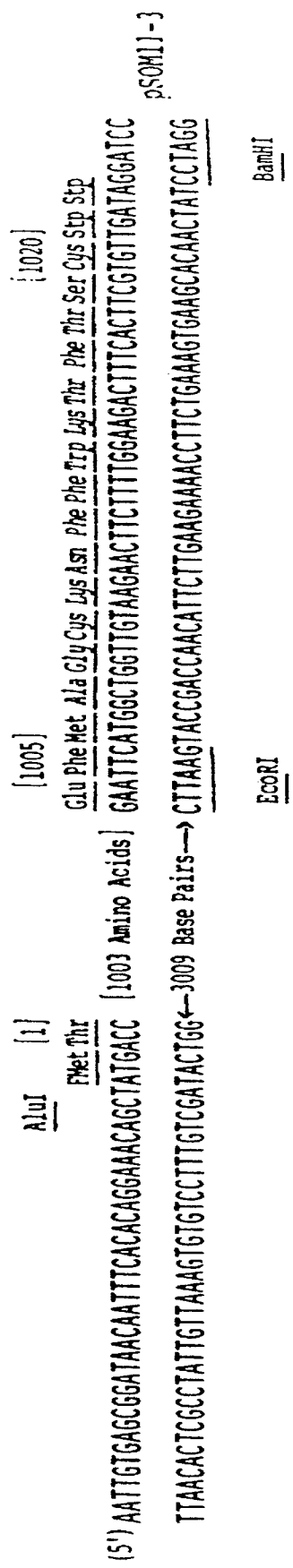
FIG 5A
FIG 5B

B-Chain Gene

```
         1   2   3   4   5   6   7   8   9  10  11  12  13  14  15  16  17  18  19  20  21  22  23  24  25  26  27  28  29  30
        Met Phe Val Asn Gln His Leu Cys Gly Ser His Leu Val Glu Ala Leu Tyr Leu Val Cys Gly Glu Arg Gly Phe Phe Tyr Thr Pro Lys Thr  stop stop
Eco RI
       AATTCATGTTCGTCAATCAGCACCTTTGTGGTTCTCACCTCGTTGAAGCTTTGTACCTTGTTTGCGGTGAACGTGGTTTCTTCTACACTCCTAAGACTTAATAG
       GTACAAGCAGTTAGTCGTGTGGAAACACCAAGAGTGGAGCAACTTCGAAACATGGAACAAACGCCACTTGCACCAAAGAAGATGTGAGGATTCTGAATTATCCTAG
                                                                Hind III                                                    Bam I
```

A-Chain Gene

```
         1   2   3   4   5   6   7   8   9  10  11  12  13  14  15  16  17  18  19  20  21
        Met Gly Ile Val Glu Gln Cys Cys Thr Ser Ile Cys Ser Leu Tyr Gln Leu Glu Asn Tyr Cys Asn  stop stop
Eco RI
       AATTCATGGGCATCGTTGAACAGTGTTGCACTAGCATCTGCTCTCTTTACCAGCTTGAGAACTACTGTAACTAATAG
       GTACCCGTAGCAACTTGTCACAACGTGAAGATAGACGAGAGAAATGGTCGAACTCTTGATGACATTGATTATCCTAG
                                                                                                                              Bam I
```

FIG 9

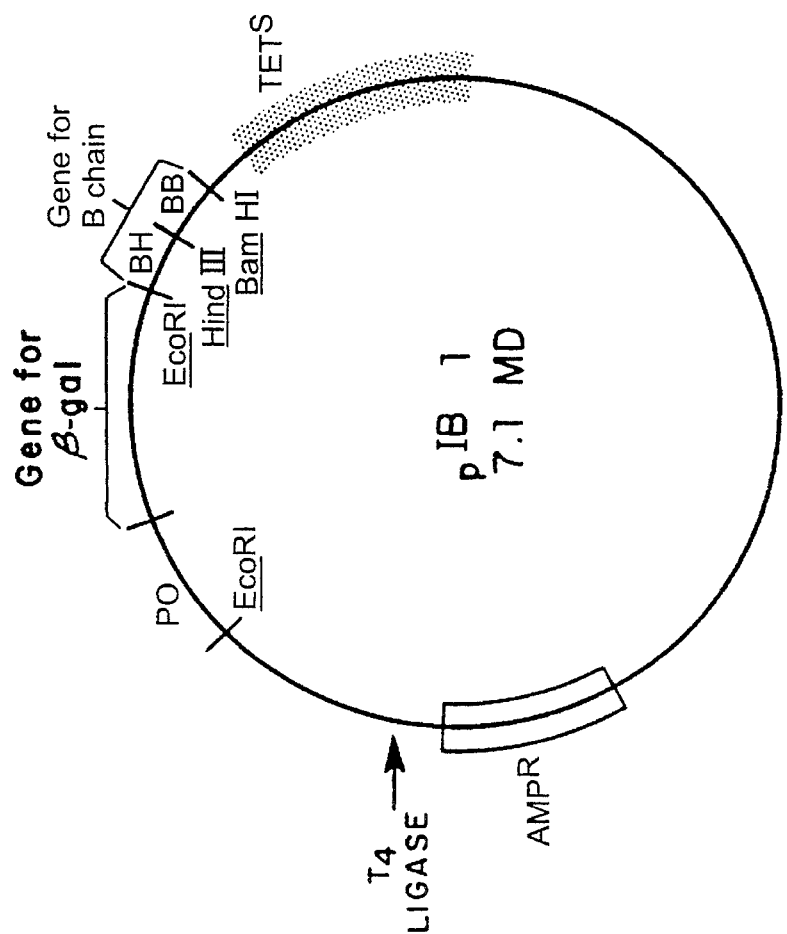
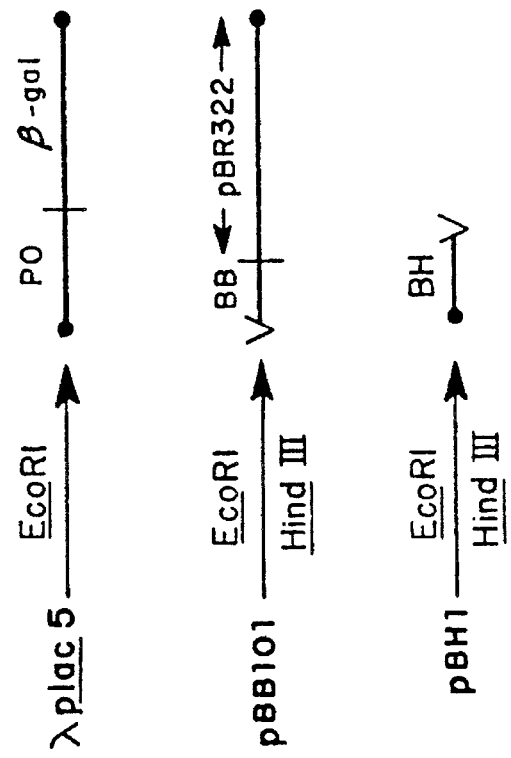
FIG 10

METHOD AND MEANS FOR MICROBIAL POLYPEPTIDE EXPRESSION

RELATED APPLICATION

This is a continuation of application Ser. No. 08/079,994 filed Jun. 18, 1993, abandoned, which is a continuation of application Ser. No. 07/821,711 filed Jan. 15, 1992, now U.S. Pat. No. 5,221,619 which is continuation of application Ser. No. 07/726,631 filed Jul. 1, 1991, abandoned, which is a continuation of application Ser. No. 07/593,488 filed Oct. 9, 1990, which is a continuation of application Ser. No. 07/317,132 filed Feb. 28, 1989, abandoned, which is a continuation of application Ser. No. 06/839,855 filed Mar. 14, 1986, abandoned, which is a continuation of application Ser. No. 06/090,979 filed Nov. 5, 1979, now U.S. Pat. No. 4,704,362 which is a continuation-in-part of application Ser. No. 05/849,692 filed Nov. 8, 1977, now U.S. Pat. No. 4,785,420.

TECHNICAL FIELD

This invention relates to a method and means for microbial polypeptide expression.

BACKGROUND

Genetic information is encoded on double-stranded deoxyribonucleic acid ("DNA" or "genes") according to the order in which the DNA coding strand presents the characteristic bases of its repeating nucleotide components. "Expression" of the encoded information to form polypeptides involves a two-part process. According to the dictates of certain control regions ("regulons") in the gene, RNA polymerase may be caused to move along the coding strand, forming messenger RNA (ribonucleic acid) in a process called "transcription." In a subsequent "translation" step the cell's ribosomes in conjunction with transfer RNA convert the mRNA "message" into polypeptides. Included in the information mRNA transcribes from DNA are signals for the start and termination of ribosomal translation, as well as the identity and sequence of the amino acids which make up the polypeptide. The DNA coding strand comprises long sequences of nucleotide triplets called "codons" because the characteristic bases of the nucleotides in each triplet or codon encode specific bits of information. For example, 3 nucleotides read as ATG (adenine-thymine-guanine) result in an mRNA signal interpreted as "start translation", while termination codons TAG, TAA and TGA are interpreted "stop translation". Between the start and stop codons lie the so-called structural gene, whose codons define the amino acid sequence ultimately translated. That definition proceeds according to the well-established "genetic code" (e.g., J. D. Watson, *Molecular Biology of the Gene* W. A. Benjamin Inc., N.Y., 3rd ed. 1976) which describes the codons for the various amino acids. The genetic code is degenerate in the sense that different codons may yield the same amino acid, but precise in that for each amino acid there are one or more codons for it and no other. Thus, for example, all of the codons TTT, TTC, TTA and TTG, when read as such, encode for serine and no other amino acid. During translation the proper reading phase or reading frame must be maintained. Consider for example what happens when the ribosome reads different bases as the beginning of a codon (underlined) in the sequence . . . GCTGGTTGTAAG . . . :

| | |
|---|---|
| . . . GCT GGT TGT AAG . . . → | . . . Ala—Gly—Cys—Lys . . . |
| . . . G CTG GTT GTA AG . . . → | . . . Leu—Val—Leu . . . |
| . . . GC TGG TTG TAA A . . . → | . . . Trp—Leu-(STOP). |

The polypeptide ultimately produced, then, depends vitally upon the spatial relationship of the structural gene with respect to the regulon.

A clearer understanding of the process of genetic expression will emerge once certain components of genes are defined:

Operon—A gene comprising structural gene(s) for polypeptide expression and the control region ("regulon") which regulates that expression.

Promoter—A gene within the regulon to which RNA polymerase must bind for initiation of transcription.

Operator—A gene to which repressor protein may bind, thus preventing RNA polymerase binding on the adjacent promoter.

Inducer—A substance which deactivates repressor protein, freeing the operator and permitting RNA polymerase to bind to promoter and commence transcription.

Catabolite Activator Protein ("CAP") Binding Site—A gene which binds cyclic adenoisine monophosphate ("c AMP")- mediated CAP, also commonly required for initiation of transcription. The CAP binding site may in particular cases be unnecessary. For example, a promoter mutation in the lactose operon of the phage Plac UV5 eliminates the requirement for cAMP and CAP expression. J. Beckwith et al, *J. Mol. Biol* 69, ISS-160 (1972).

Promoter-Operator System—As used herein, an operable control region of an operon, with or without respect to its inclusion of a CAP binding site or capacity to code for repressor protein expression.

Further by way of definition, and for use in the discussion of recombinant DNA which follows, we define the following:

Cloning Vehicle—Non-chromosomal double stranded DNA comprising an intact "replicon" such that the vehicle is replicated, when placed within a unicellular organism ("microbe") by a process of "transformation". An organism so transformed is called a "transformant".

Plasmid—For present purposes, a cloning vehicle derived from viruses or bacteria, the latter being "bacterial plasmids."

Complementarity—A property conferred by the base sequences of single strand DNA which permits the formation of double stranded DNA through hydrogen bonding between complementary bases on the respective strands. Adenine (A) complements thymine (T), while guanine (G) complements cytosine (C).

Advances in biochemistry in recent years have led to the construction of "recombinant" cloning vehicles in which, for example, plasmids are made to contain exogenous DNA. In particular instances the recombinant may include "heterologous" DNA, by which is meant DNA that codes for polypeptides ordinarily not produced by the organism susceptible to transformation by the recombinant vehicle. Thus, plasmids are cleaved to provide linear DNA having ligatable termini. These are bound to an exogenous gene having ligatable termini to provide a biologically functional moiety with an intact replicon and a desired phenotypical property. The recombinant moiety is inserted into a microorganism by transformation and transformants are isolated and cloned, with the object of obtaining large populations capable of expressing the new genetic information. Methods and means of forming recombinant cloning vehicles and transforming organisms with them have been widely reported in the literature. See, e.g., H. L. Heynecker et al, *Nature* 263, 748–752 (1976) Cohen et al, *Proc. Nat. Acad. Sci. U.S.A* 69, 2110 (1972); ibid., 70, 1293 (1973); ibid., 70 3240 (1973); ibid., 71, 1030 (1974) Morrow et al, *Proc. Nat. Acad. Sci. U.S.A.* 71, 1743 (1974) Novick, *Bacteriological Rev.,* 33, 210 (1969); Hershfel et al, *Proc. Soc. Nat'l. Acad. Sci. U.S.A.* 71, 3455 (1974) and Jackson et al, ibid. 69, 2904 (1972). A generalize discussion of the subject appears in S. Cohen, *Scientific American* 233, 24 (1975). These and other publications alluded to herein are incorporated by reference.

A variety of techniques are available for DNA recombination, according to which adjoining ends of separate DNA fragments are tailored in one way or another to facilitate ligation. The latter term refers to the formation of phosphodiester bonds between adjoining nucleotides, most often through the agency of the enzyme T4 DNA ligase. Thus, blunt ends may be directly ligated. Alternatively, fragments containing complementary single strands at their adjoining ends are advantaged by hydrogen bonding which positions the respective ends for subsequent ligation. Such single strands, referred to as cohesive termini, may be formed by the addition of nucleotides to blunt ends using terminal transferase, and sometimes simply by chewing back one strand of a blunt end with an enzyme such λ-exonuclease. Again, and most commonly, resort may be had to restriction endonucleases, which cleave phosphodiester bonds in and around unique sequences of nucleotides of about 4–6 base pairs in length. Many restriction endonucleases and their recognition sites are known, the so-called Eco RI endonuclease being most widely employed. Restriction endonucleases which cleave double-stranded DNA at rotationally symmetric "palindromes" leave cohesive termini. Thus, a plasmid or other cloning vehicle may be cleaved, leaving termini each comprising half the restriction endonuclease recognition site. A cleavage product of exogenous DNA obtained with the same restriction endonuclease will have ends complementary to those of the plasmid termini. Alternatively, as disclosed infra, synthetic DNA comprising cohesive termini may be provided for insertion into the cleaved vehicle. To discourage rejoinder of the vehicles' cohesive termini pending insertion of exogenous DNA, the termini can be digested with alkaline phosphatase, providing molecular selection for closures incorporating the exogenous fragment. Incorporation of a fragment having the proper orientation relative to other aspects of the vehicle may be enhanced when the fragment supplants vehicle DNA excised by two different restriction endonucleases, and itself comprises termini respectively constituting half the recognition sequence of the different endonucleases.

Despite wide-ranging work in recent years in recombinant DNA research, few results susceptible to immediate and practical application have emerged. This has proven especially so in the case of failed attempts to express polypeptides and the like coded for by "synthetic DNA", whether constructed nucleotide by nucleotide in the conventional fashion or obtained by reverse transcription from isolated mRNA (complementary or "cDNA"). In this application we describe what appears to represent the first expression of a functional polypeptide product from a synthetic gene, together with related developments Which promise widespread application. The product referred to is somatostatin (Guillemin U.S. Pat. No. 3,904,594), an inhibitor of the secretion of growth hormone, insulin and glucagon whose effects suggest its application in the treatment of acromegaly, acute pancreatitis and insulin-dependent diabetes. See R. Guillemin et al, *Annual Rev.* Med. 27 379 (1976). The somatostatin model clearly demonstrates the applicability of the new developments described here on numerous and beneficial fronts, as will appear from the accompanying drawings and more clearly from the detailed description which follows.

SUMMARY OF INVENTION

According to the invention there is provided a recombinant plasmid suited for transformation of a bacterial host and use therein as a cloning vehicle, wherein the plasmid comprises:

a) A regulon homologous to the bacterial host in its untransformed state; and b) In reading phase with the regulon, a DNA insert coding for the amino acid sequence of a heterologous polypeptide, such that bacteria transformed by the plasmid are capable of expressing said amino acid sequence in recoverable form.

BRIEF DESCRIPTION OF THE DRAWINGS

The accompanying drawings illustrate one context in which preferred embodiments of the invention find application, i.e., expression of the hormone somatostatin by bacterial transformants containing recombinant plasmids.

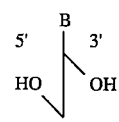

Figure 4:
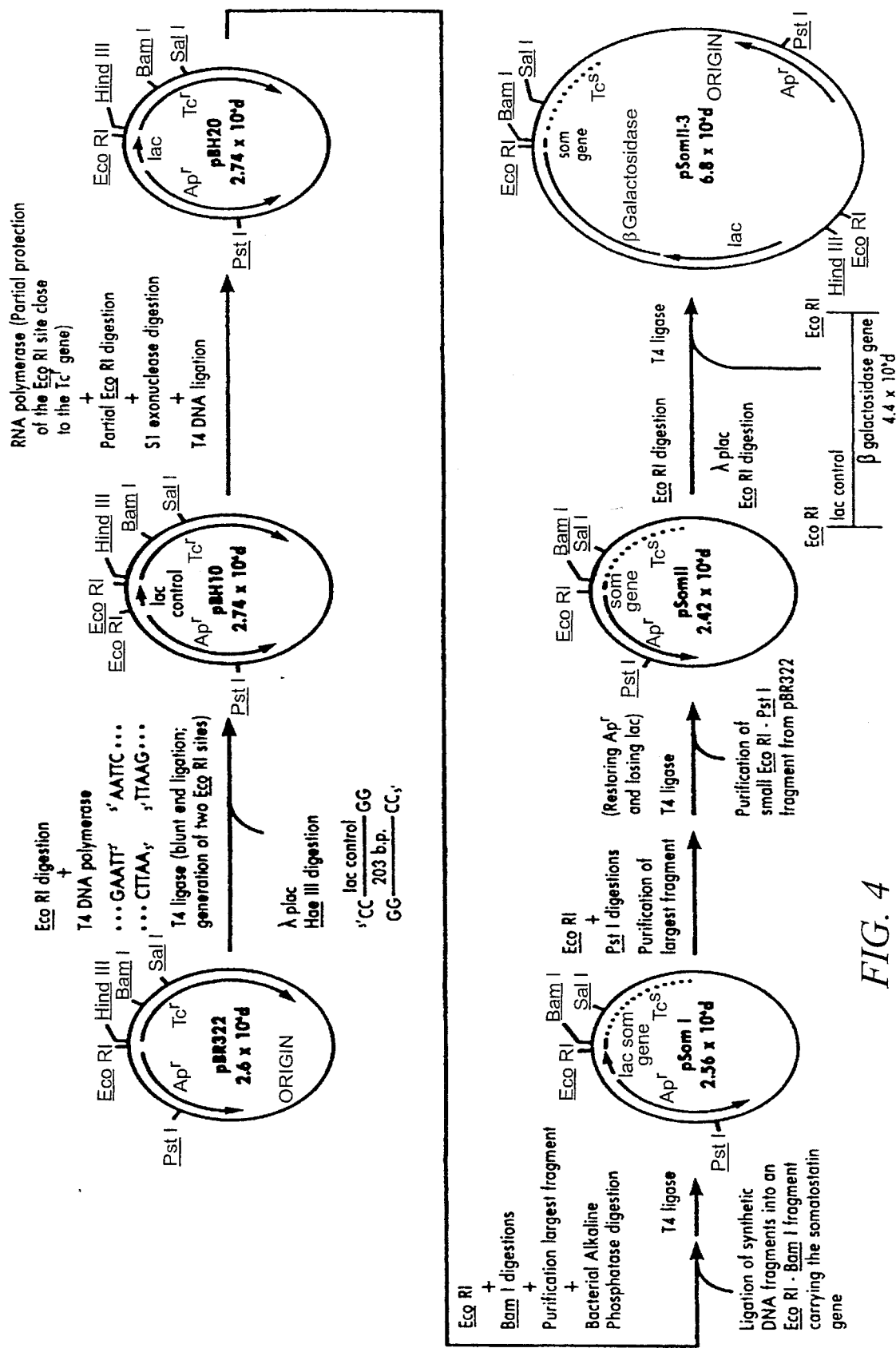

FIG. 4. Flow chart for the construction of a recombinant plasmid (e.g., pSOM11-3) capable of expressing a somatostatin ("SOM") - containing protein, beginning with the parental plasmid pBR322. In FIG. 4 the approximate molecular weight of each plasmid is stated in daltons ("d").

Ap^r and Tc^r respectively denote genes for epicillin and tetracycline resistance, while Tc^s denotes tetracycline susceptibility resulting from excision of a portion of the Tc^r gene. The relative positions of various restriction endonuclease specific cleavage sites on the plasmids are depicted (e.g., Eco RI, Bam I, etc.).

FIGS. 5A and 5B. The nucleotide sequences of key portions of two plasmids are depicted, as is the direction of messenger RNA ("mRNA") transcription, which invariably proceeds from the 5' end of the coding strand. Restriction endonuclease substrate sites are as shown. Each depicted sequence contains both the control elements of the lac (lactose) operon, and codons for expression of the amino acid sequence of somatostatin (italics). The amino acid sequence numbers for β-galactosidase ("β-gal") are in brackets.

Figure 6:
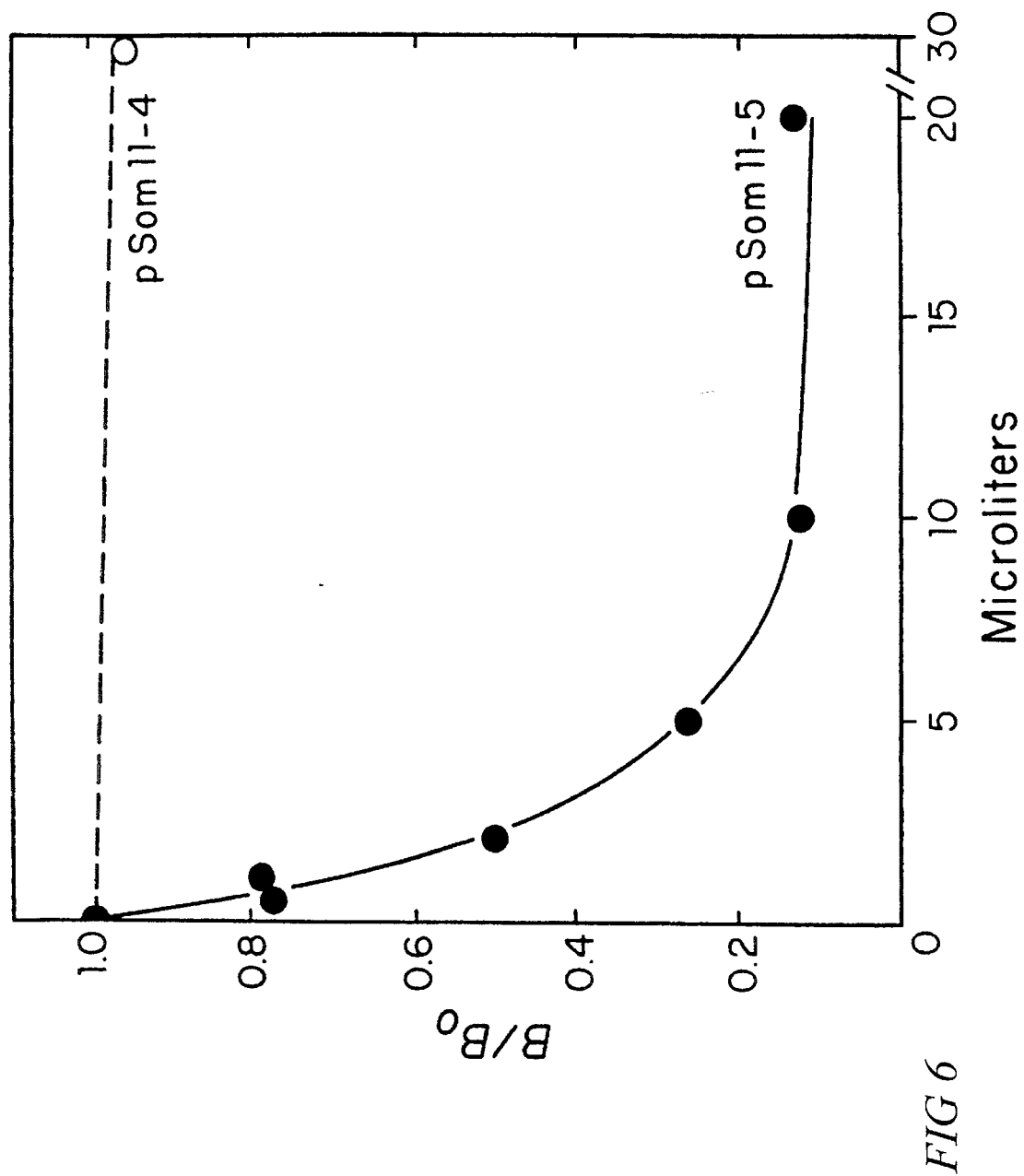
Figure 7:
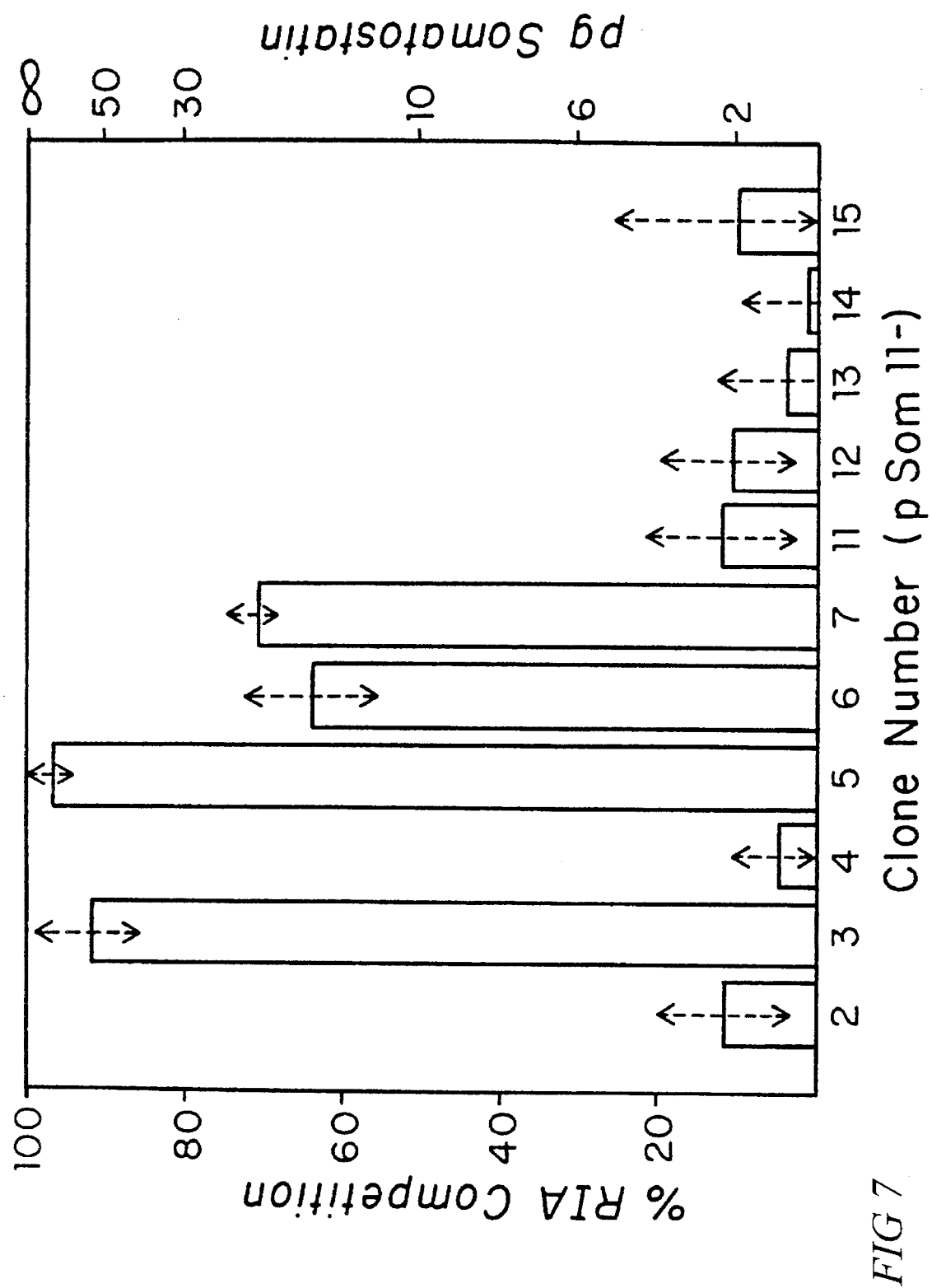
Figure 8:
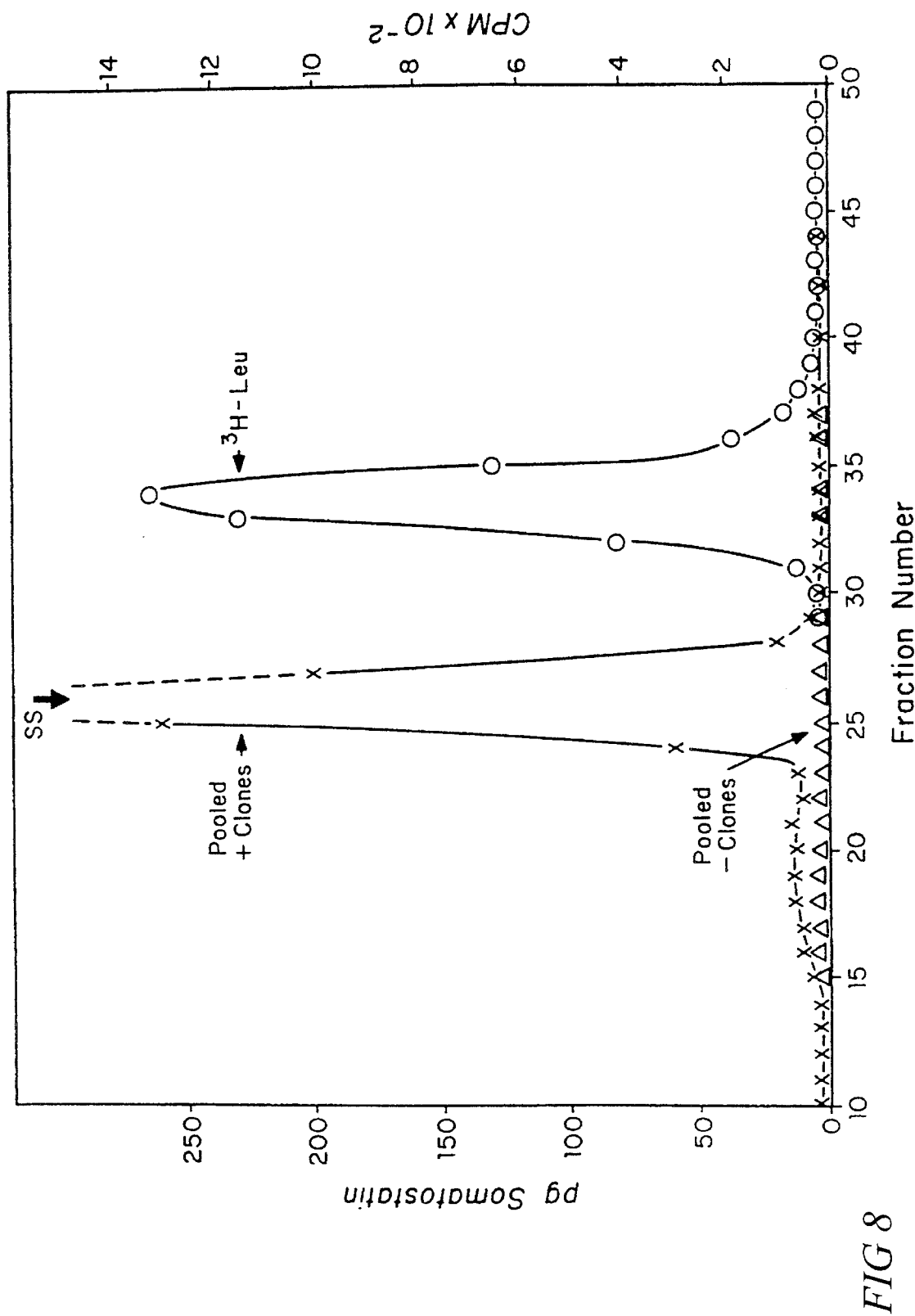

FIGS. 6, 7, and 8. As more particularly described in the "Experimental" discussion, infra, these depict the results of comparative radioimmune assay experiments which demonstrate the somatostatin activity of product expressed by the recombinant plasmids.

FIG. 9. Schematic structure of synthetic genes whose coding strands comprise codons for the amino acid sequences of the A and B strands of human insulin.

FIG. 10. Flow chart for construction of a recombinant plasmid capable of expressing the B chain of human insulin.

DETAILED DESCRIPTION

1. Preparation of Genes Coding for Heterologous Polypeptide

DNA coding for any polypeptide of known amino acid sequence may be prepared by choosing codons according to the genetic code. For ease in purification, etc., oligodeoxyribonucleotide fragments of, for example, from about 11 to about 16 nucleotides are prepared separately, then assembled in the desired sequence. Thus, one prepares first and second series of oligodeoxyribonucleotide fragments of convenient size. The first series, when joined in proper sequence, yield a DNA coding strand for polypeptide expression (see, e.g., FIG. 2, fragments A, B, C and D). The second series, when likewise joined in proper sequence, yield a strand complementary to the coding strand (e.g., FIG. 2, fragments E, F, G and H). The fragments of the respective strands preferably overlap such that complementarity promotes their self assembly through hydrogen bonding of the cohesive terminii of fragment blocks. Following assembly, the structural gene is completed by ligation in the conventional manner.

The degeneracy of the genetic code permits substantial freedom in the choice of codons for any given amino acid sequence. For present purposes, however, codon choice was advantageously guided by three considerations. First, codons and fragments were selected, and fragment assembly was staged, so as to avoid undue complementarity of the fragments, one with another, save for fragments adjacent one another in the intended gene. Secondly, sequences rich in AT base pairs (e.g., about five or more) are avoided, particularly when preceded by a sequence rich in GC base pairs, to avoid premature termination of transcription. Thirdly, at least a majority of the codons chosen are those preferred in the expression of microbial genomes (see, e.g., W. Fiefs, et al, *Nature* 260, 500 (1976). For purposes of the appended claims, we define the following as codons "preferred for the expression of microbial genomes":

TABLE I

PREFERRED ASSIGNMENT OF CODONS

| First Position (5' End) (Read Down) | Second Position (Read Across) | | | | Third Position (3' End) (Read Down) |
|---|---|---|---|---|---|
| | T | C | A | G | |
| T | phe | — | — | cys | T |
| | phe | ser | tyr | — | C |
| | leu | — | Stop | Stop | A |
| | — | ser | Stop | trp | G |
| C | leu | pro | his | arg | T |
| | leu | pro | his | arg | C |
| | leu | pro | gln | — | A |
| | — | pro | gln | — | G |
| A | ile | thr | asn | — | T |
| | ile | thr | asn | ser | C |
| | — | — | — | — | A |
| | met (start) | thr | lys | — | G |
| G | val | ala | asp | gly | T |
| | val | — | asp | — | C |
| | val | — | glu | — | A |
| | val | ala | glu | — | G |

Figure 1:
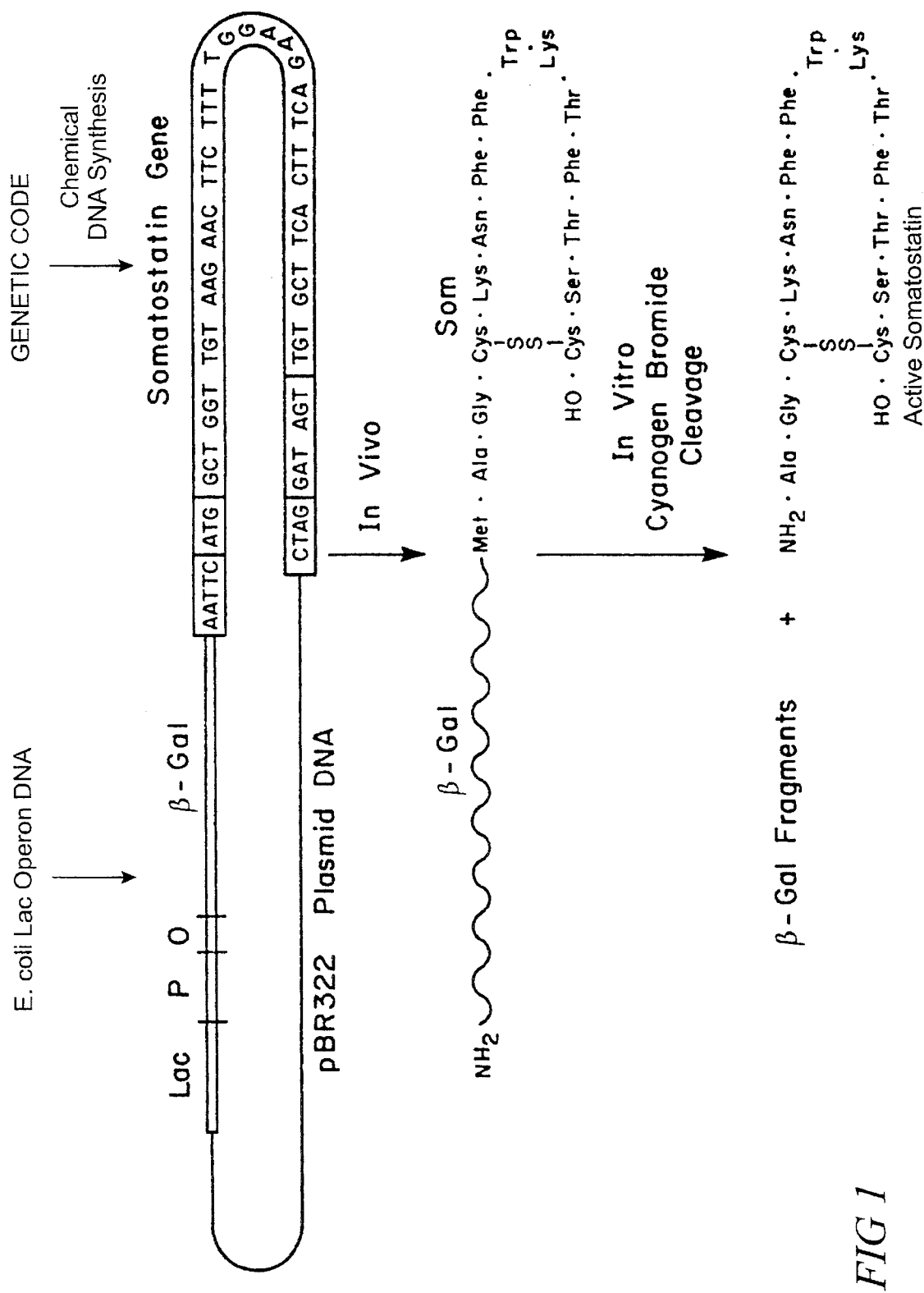
FIG. 1. Schematic outline of the process: the gene for somatostatin, made by chemical DNA synthesis, is fused to the *E. coli* β-galactosidase gene on the plasmid pBR322. After transformation into *E. coli*, the recombinant plasmid directs the synthesis of a precursor protein which can be specifically cleaved in vitro at methionine residues by cyanogen bromide to yield active mammalian polypeptide hormone. A, T, C and G denote the characteristic bases (respectively adeninc, thymine, cytosine and guanine) of the deoxyribonucleotides in the coding strand of the somatostatin gene.
Figure 2:
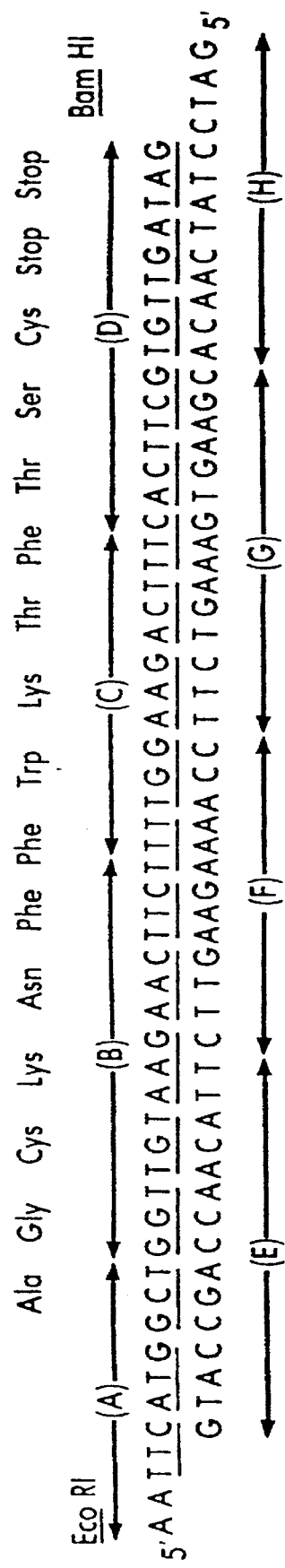
FIG. 2. Schematic structure of a synthetic gene whose coding strand (i.e., the "upper" strand) comprises codons for the amino acid sequence of somatostatin (given).

Most preferably in the case of somatostatin, the amino acid (codon) relationships of the structural gene are: gly (GGT); cys (TGT); lys (AAG); trp (TGG); ala (GCT, GCG); ash (AAT, AAC); phe (TTC, TTT); thr (ACT, ACG); and set (TCC, TCG).

Where the structural gene of a desired polypeptide is to be inserted in a cloning vehicle for expression as such, the gene is preceded by a "start" codon (e.g., ATG) and immediately followed by one or more termination or stop codons (see FIG. 2). However, as described infra, the amino acid sequence of a particular polypeptide may be expressed with additional protein preceding and/or following it. If the intended use of the polypeptide requires cleavage of the additional protein, appropriate cleavage sites are coded for adjacent the polypeptide-additional protein codon junction. Thus, in FIG. 1 as an example, the expression product is a precursor protein comprising both somatostatin and the greatest part of the β-galactosidase polypeptide. Here ATG is not required to code for the start of translation because ribosomal translation of the additional β-gal protein reads through into the somatostatin structural gene. Incorporation of the ATG signal, however, codes for the production of methionine, an amino acid specifically cleaved by cyanogen bromide, affording a facile method for converting precursor protein into the desired polypeptide.

FIG. 2 also exemplifies a further feature preferred in heterologous DNA intended for recombinant employment, i.e., the provision of cohesive termini, preferably comprising one of the two strands of a restriction endonuclease recognition site. For reasons previously discussed, the terminii are preferably designed to create respectively different recognition sites upon recombination.

While the developments described here have been demonstrated as successful with the somatostatin model, it will be appreciated that heterologous DNA coding for virtually any known amino acid sequence may be employed, mutatis mutandis. Thus, the techniques previously and hereafter discussed are applicable, mutatis mutandts, to the production of poly(amino)acids, such as polyleucine and polyalanine; enzymes; serum proteins; analgesic polypeptides, such as β-endorphins, which modulate thresholds of pain, etc. Most preferably, the polypeptides produced as such will be mammalian hormones or intermediates therefor. Among such hormones may be mentioned, e.g., somatostatin, human insulin, human and bovine growth hormone, leutinizing hormone, ACTH, pancreatic polypeptide, etc. Intermediates include, for example, human preproinslin human proinsulin, the A and B chains of human insulin and so on. In addition to DNA made in vitro, the heterologous DNA may comprise DNA resulting from reverse transcription from mRNA. See, e.g., Ullrich et al, *Science* 196, 1313 (1977).

2. Recombinants Coding for the Expression of Precursor Protein

In the process schematically depicted in FIG. 1, expression yields a precursor protein comprising both a polypeptide coded for by a specific heterologous structural gene (somatostatin) and additional protein (comprising a portion of the β-galactosidase enzyme). A selective cleavage site adjacent the somatostatin amino acid sequence permits subsequent separation of the desired polypeptide from superfluous protein. The case illustrated is representative of a large class of procedures made available by the techniques described herein.

Most commonly, cleavage will be effected outside the replicative environment of the Plasmid or other vehicle as, for example, following harvest of the microbial culture. In this fashion temporary conjugation of small polypeptides with superfluous protein may preserve the former against, e.g., in vivo degradation by endogenous enzymes. At the same time, the additional protein will ordinarily rob the desired polypeptide of bioactivity pending extra-cellular cleavage, with the effect of enhancing the biosafety of the procedure. In particular instances, of course, it may prove desirable to effect cleavage within the cell. For example, cloning vehicles could be provided with DNA coding for enzymes which convert insulin precursors to the active form, operating in tandem with other DNA coding for expression of the precursor form.

In the preferred case, the particular polypeptide desired lacks internal cleavage sites corresponding to that employed to shed superfluous protein, although it will be appreciated that where that condition is not satisfied competition reactions will yet give the desired product, albeit in lower yield. Where the desired product is methionine-free, cyanogen bromide cleavage at methionine adjacent the desired sequence has proven highly effective. Likewise, arginine- and lysine-free products may be enzymatically cleaved with, e.g., trypsin or chymotrypsin at arg-arg, lys-lys or like cleavage sites adjacent the desired sequence. In the case where cleavage leaves, e.g., unwanted arginine attached to desired product, it may be removed by carboxypeptidase digestion. When trypsin is employed to cleave at arg-arg, lysine sites within the desired polypeptide may first be protected, as with maleic or citraconic anhydrides. The cleavage techniques discussed here by way of example are but representative of the many variants which will occur to the art-skilled in light of the specification.

Cleavable protein may be expressed adjacent either the C- or N-terminals of a specific polypeptide, or even within the polypeptide itself, as in the case of the included sequence which distinguishes proinsulin and insulin. Again, the vehicle employed may code for expression of protein comprising repeated sequences of the desired polypeptide, each separated by selective cleavage sites. Most preferably, however, codons for superfluous protein will be translated in advance of the structural gene of the desired product, as in the case illustrated in the Figures. In every case care should be taken to maintain the proper reading frame relative to the regulon.

3. Expression of Immunogens

The ability to express both a specific polypeptide and superfluous protein provides useful tools for the production of immunogenic substances. Polypeptide "haptens" (i.e. substances containing determinants specifically bound by antibodies and the like but ordinarily too small to elicit an immune response) can be expressed as conjugates with additional protein sufficient in size to confer immunogenicity. Indeed, the β-gal- somatostatin conjugate produced here by way of example is of immunogenic size and may be expected to raise antibodies which bind the somatostatin hapten. Proteins comprising in excess of 100 amino acids, most commonly in excess of 200 such, exhibit immunogenic character.

Conjugates prepared in the foregoing fashion may be employed to raise antibodies useful in radioimmune or other assays for the hapten, and alternatively in the production of vaccines. We next describe an example of the latter application. Cyanogen bromide—or other cleavage products of vital coat protein will yield oligopeptides which bind to antibody raised to the protein itself. Given the amino acid sequence of such an oligopeptide hapten, heterologous DNA therefore may be expressed as a conjugate with additional protein which confers immunogenicity. Use of such conjugates as vaccines could be expected to diminish side reactions which accompany use of coat protein itself to confer immunity.

4. The Control Elements

FIG. 1 depicts a process wherein a transformant organism expresses polypeptide product from heterologous DNA brought under the control of a regulon "homologous" to the organism in its untransformed state. Thus, lactose-dependent *E. Coli.* chromosomal DNA comprises a lactose or "lac" operon which mediates lactose digestion by, inter alia, elaborating the enzyme β-galactosidase. In the particular instance illustrated, the lac control elements are obtained from a bacteriophage, λ plac 5, which is infective for the *E. Coli.* The phage's lac operon, in turn, was derived by transduction from the same bacterial species, hence the "homology". Homologous regulons suitable for use in the disclosed process may alternatively derive from plasmidic DNA native to the organism.

The simplicity and efficiency of the lac promoteroperator system commend its use in the systems we describe, as does its ability to be induced by IPTG (isopropylthio-β-D galactoside). Of course, other operons or portions thereof could be employed as well, e.g., lambda promoter-operator, arabinose operon (phi 80 data), or the colicine El, galactose, alkaline phosphatase or tryptophan operons. Promoter-operators derived from the latter (i.e., "tryp (or trp) operon") would be expected to confer 100% repression pending induction (with indoleacrylic acid) and harvest.

5. Plasmid Construction Generally

The details of the process schematically illustrated in FIG. 4 appear from the Experimental section, infra. At this point, however, it is useful to briefly discuss various of the techniques employed in constructing the recombinant plasmid of the preferred embodiment.

The cloning and expression of the synthetic somatostatin gene employed two plasmids. Each plasmid has an EcoRI substrate site at a different region of the β-galactosidas structural gene (see FIGS. 4 and 5). The insertion of the synthetic somatostatin DNA fragment into the EcoRI sites of these plasmids brings the expression of the genetic information in that fragment under control of the lac operon controlling elements. Following the insertion of the somatostatin fragment into these plasmids, translation should result in a somatostatin polypeptide preceded either by 10 amino acid (pSOM1) or by virtually the whole β-galactosidase subunit structure (pSOM11-3).

The plasmid construction scheme initiates with plasmid pBR322, a well-characterized cloning vehicle. Introduction of the lac elements to this plasmid was accomplished by insertion of a HaeIII restriction endonuclease fragment (203 nucleotides) carrying the lac promoter, CAP binding site, operator, ribosome binding site, and the first 7 amino acid codons of the β-galactosidase structural gene. The HaeIII fragment was derived from λ plac5 DNA. The EcoRI-cleaved PBR322 plasmid, which had its termini repaired with T4 DNA polymerase and deoxyribonucleotide triphosphates, was blunt-end ligated to the HaeIII fragment to create EcoRI termini at the insertion points. Joining of these HaeIII and repaired EcoRI termini generate the EcoRI restriction site (see FIG. 4 and 5) at each terminus. Transformants of *E. Coli* RR1 with this DNA were selected for resistance to tetracycline (Tc) and ampicillin (Ap) on 5-bromo-4-chloro-incolylgalactoside (X-gal) medium. On this indicator medium, colonies constitutive for the synthesis of β-galactosidase, by virtue of the increased number of lac operators titrating repressor, are identified by their blue color. Two orientations of the HaeIII fragment are possible but these were distinguished by the asymmetric location of an Hha restriction site in the fragment. Plasmid pBH10 was further modified to eliminate the EcoRI endonuclease site distal to the lac operator (pBH20).

The eight chemically synthesized oligodeoxyribonucleotides (FIG. 2) were labeled at the 5' termini with $[^{32}P]$-γ-ATP by polynucleotide kinase and joined with T4 DNA ligase. Through hydrogen bonding between the overlapping fragments, the somatostatin gene self-assembles and eventually polymerizes into larger molecules because of the cohesive restriction site termini. The ligated products were treated with EcoRI and BamHI restriction endonucleases to generate the somatostatin gene as depicted in FIG. 2.

The synthetic somatostatin gene fragment with EcoRI and BamHI termini was ligated to the pBH20 plasmid, previously treated with the EcoRI and BamHI restriction endonucleases and alkaline phosphatase. The treatment with alkaline phosphatase provides a molecular selection for plasmids carrying the inserted fragment. Ampicillin-resistant transformants obtained with this ligated DNA were screened for tetracycline sensitivity and several were examined for the insertion of an EcoRI-BamHI fragment of the appropriate size.

Both strands of the EcoRI-BamHI fragments of plasmids from two clones were analyzed by nucleotide sequence analysis starting from the BamHI and EcoRI sites. The sequence analysis was extended into the lac controlling elements; the lac fragment sequence was intact, and in one case, pSOM1, the nucleotide sequence of both strands were independently determined each giving the sequence depicted in FIG. 5A.

The EcoRI-Pst fragment of the pSOM1 plasmid, with the lac-controlling element, was removed and replaced with the EcoRI-Pst fragment of pBR322 to produce the plasmid pSOM11. The EcoRI fragment of λ plac 5, carrying the lac operon control region and most of the β-galactosidase structural gene, was inserted into the EcoRI site of pSOM11. Two orientations of the EcoRI lac fragment of plac 5 were expected. One of these orientations would maintain the proper reading frame into the somatostatin gene, the other would not. Analysis of independently isolated clones for somatostatin activity then identified clones containing the properly oriented gene, of which the clone designated pSOM11-3 was one.

6. The Microorganism

Various unicellular microorganisms have been proposed as candidates for transformation, such as bacteria, fungii and algae. That is, those unicellular organisms which are capable of being grown in cultures or fermentation. Bacteria are for the most part the most convenient organisms to work with. Bacteria which are susceptible to transformation include members of the Enterobacteriaceae, such as strains of Escherichia coli and Salmonella; Bacillaceae, such as Bacillus subtillis; Pneumococcus; Streptococcus, and Haemophilus influenzae.

The particular organism chosen for the somatostatin work next discussed was *E.Coli.* strain RR1, genotype: Pro$^-$Leu$^-$ Thi$^-$R$_B$$^-$M$_B$ $\overline{\text{rec}}$ A$^+$ Str$^r$ Lac y$^-$ *E. coli.* RR1 is derived from *E. Coli.* HB101 (H. W. Boyer, et al; J. Mol. Biol. (1969) 41, 459–472) by mating with *E. Coli* K12 strain KL16 as the Hfr donor. See J. H. Miller, Experiments in Molecular Genetics (Cold Spring Harbor, N.Y., 1972). Cultures of both *E. Coli* RR1 and *E. Coli.* RR1 (pBR322) have been deposited with the American Type Culture Collection without restriction as to access, respectively ATCC Nos. 31343 and 31344. The somatostatin-producing organism has likewise been deposited [ATCC No. 31447].

In the case of human insulin, A and B chain genes were cloned in *E. Coli* K-12 strain 294 (end A, thi$^-$, hsr$^-$, hsm$_k^+$), ATCC No. 31446, and that organism employed in expression of the A chain (*E. Coli* K-12 strain 294 [pIA1], ATCC No. 31448). The B chain of human insulin was first expressed in a derivative of HB101, i.e., *E. coli* K-12 strain D1210 a lac$^+$ (i$^Q$o$^+$z'y$^+$), and that B gene-containing organism has likewise been deposited (ATCC No. 31449). Alternatively, the B gene may be inserted in and expressed from the organism first mentioned, i.e., strain 294.

EXPERIMENTAL

I SOMATOSTATIN

1. Construction of Somatostatin Gene Fragments

Figure 3:
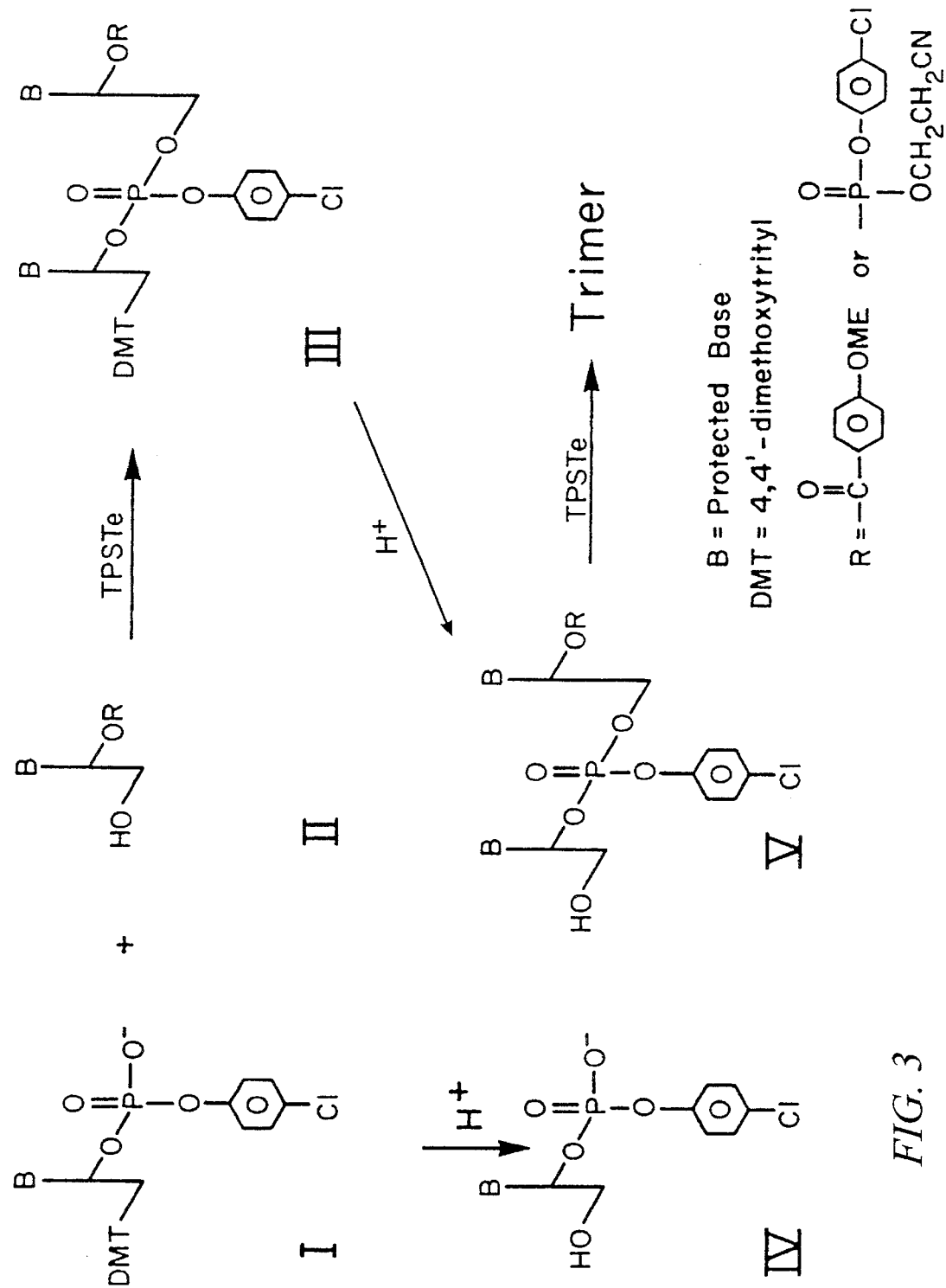
FIG 3. Schematic illustration of preferred method for construction of nucleotide trimers used in constructing synthetic genes. In the conventional notation employed to depict nucleotides in FIG. 3, the 5' OH is to the left and the 3' OH to the right, e.g.

Eight oligodeoxyribonucleotides respectively labeled A through H in FIG. 2 were first constructed, principally by the modified triester method of K. Itakura et al, *J. Am. Chem. Soc.* 97, 7327 (1975). However, in the case of fragments C, E and H resort was had to an improved technique in which fully protected trimers are first prepared as basic units for building longer oligodeoxyribonucleotides. The improved technique is schematically depicted in FIG. 3, wherein B is thymine, N-benzoylated adenine; N-benzoylated cytosine or N-isobutyrulated guanine. In brief, and with reference to FIG. 3, with an excess of I (2 mmole), the coupling reaction with II (1 mmole) went almost to completion in 60 rain with the aid of a powerful coupling reagent, 2,4,6-triisopropyl-benzenesulfonyl tetrazolide (TPSTe, 4 mmole; 2). After removal of the 5'-protecting group with 2% benzene sulfonic acid solution, the 5'-hydroxyl dimer V could be separated from an excess of 3'-phosphodiester-monomer IV by simple solvent extraction with aqueous NaHCO$_3$ solution in CBCl$_3$. The fully protected trimer block was prepared successively from the 5'-hydroxyl dimer V, I (2 mole), and TPSTe (4 mmole) and isolated by chromatography on silica gel, as in B. T. Hunt et al, *Chem. and Ind.* 1967, 1868 (1967). The yields of trimers made according to the improved technique appear from Table II.

TABLE II

Yields of Fully Protected Trimers

| Sequence | Yield | Sequence | Yield |
|---|---|---|---|
| TTT | 81% | ATG | 69% |
| TTT | 75% | GCC | 61% |
| GGA | 41% | CCA | 72% |
| AGA | 49% | CAA | 72% |
| ATC | 71% | TTA | 71% |
| CCT | 61% | CAT | 52% |
| ACA | 63% | CCC | 73% |
| ACC | 65% | AAC | 59% |
| CGT | 51% | GAT | 60% |

The eight oligodeoxyribonucleotides, after removal of all protecting groups, were purified by high-pressure liquid chromatography on Permaphase AAX (R. A. Henry et al *J. Chrom. Sci. II*, 358 (1973)). The purity of each oligomer was checked by homochromatography on thin-layer DEAE-cellulose and also by gel electrophoresis in 20% acrylamide slab after labeling of the oligomers with [γ-$^{32}$P]-ATP in the presence of polynucleotide kinase. One major labeled product was obtained from each DNA fragment.

2. Ligation and Acrylamide Gel Analysis of Somatostatin DNA

The 5' OH termini of the chemically synthesized fragments A through H were separately phosphorylated with T4 polynucleotide kinase. [$^{32}$P]-γ-ATP was used in phosphorylation so that reaction products could be monitored autoradiographically, although it will be appreciated that unlabelled ATP would serve as well were autoradiography dispensed with. Just prior to the kinase reaction, 25 uCi of [γ-$^{32}$P]ATP (approx. 1500 Ci/mMol) (Maxam and Gilbert, *Proc. Nat. Acad. Sci. U.S.A.* 74, 1507 (1977) was evaporated to dryness in 0.5 ml Eppendorf tubes. Five micrograms of fragment were incubated with 2 units of T4 DNA kinase (hydroxylapatite fraction, 2500 units/ml), in 70 mM Tris-HCl pH 7.6, 10 mM MgCl$^2$, 5 mM dithiothreitol in a total volume of 150 μl for 20 min at 37° C. To insure maximum phosphorylation of the fragments for ligation purposes, 10 μl of a mixture consisting of 70 mM Tris-HCl pH 7.6, 10 mM MgCl$_2$, 5 mM dithothreitol, 0.5 mM ATP and two units of DNA kinase were added and incubation continued for an additional 20 min at 7° C. The fragments (250 ng/μl) were stored at –20° C. without further treatment. Kinased fragments A, B, E, and F (1.25 μg each) were ligated in a total volume of 50 μl in 20 mM Tris-HCl pH 7.6, 10 mM Mg Cl$_2$, 10 mM dithiothreitol, 0.5 mM ATP and 2 units of T4 DNA ligase (hydroxylapatite fraction, 400 units/ml; 27), for 16 hr at 4° C. Fragments C, D, G and H were ligated under similar conditions. Samples of 2 μl were removed for analysis by electrophoresis on a 10% polyacrylamide gel followed by autoradiography (H. L. Heyneker et al, *Nature* 263, 748 (1976)) in which unreacted DNA fragments are represented by fast migrating material and wherein the monomeric form of the ligated fragments migrate with bromophenol blue dye (BPB). Some dimerization also occurs by reason of the cohesive ends of the ligated fragments A, B, E and F, and of the ligated fragments C, D, G and H. These dimers represent the slowest migrating material, and may be cleaved by restriction endonuclease EcoRI and BamHI, respectively.

The two half molecules (ligated A+B+E+F and ligated C+D+G+H) were joined by an additional ligation step carried out in a final volume of 150 μl at 4° C. for 16 hr. One microliter was removed for analysis. The reaction mixture was heated for 15 min at 65° C. to inactivate the T4 DNA ligase. The heat treatment does not affect the migration pattern of the DNA mixture. Enough restriction endonuclease BamHI was added to the reaction mixture to cleave the multimeric forms of the somatostatin DNA in 30 min at 37° C. After the addition of NaCl to 100 mM, the DNA was digested with EcoRI endonuclease. The restriction endonuclease digestions were terminated by phenol-chloroform extraction of the DNA. The somatostatin DNA fragment was purified from unreacted and partially ligated DNA fragments by preparative electrophosresis on a 10% polyacrylamide gel. The band containing the somatostatin DNA fragment was excised from the gel and the DNA was eluted by slicing the gel into small pieces and extracting the DNA with elution buffer (0.5M ammonium acetate, 10 mM MgCl$_2$, 0.1 mM EDTA, 0.1% SDS) overnight at 65° C. The DNA was precipitated with 2 volumes of ethanol, centrifuged, redissolved in 200 μl 10 mM Tris-HCl pH 7.6 and dialyzed against the same buffer resulting in a somatostatin DNA concentration of 4 μg/ml.

3. Construction of Recombinant Plasmids

FIG. 4 schematically depicts the manner in which recombinant plasmids comprising the somatostatin gene were constructed, and may be referred to in connection with the following more particularized discussion.

A. The Parental Plasmid pBR322

The plasmid chosen for experimental somatostatin cloning was pBR322, a small (molecular wt. approx. 2.6 megadaltons) plasmid carrying resistance genes to the antibiotics ampicillin (Ap) and tetracycline (Tc). As indicated in FIG. 4, the ampicillin resistance gene includes a cleavage site for the restriction endonuclease Pst I, the tetracycline resistance gene includes a similar site for restriction endonuclease BamHI, and an EcoRI site is situated between the Ap$^r$ and TC$^r$ genes. The plasmid pBR322 is derived from pBR313, a 5.8 megadalton Ap$^r$Tc$^r$Col$^{imm}$ plasmid (R. L. Rodriguez et al, ICN-UCLA Symposia on Molecular and Cellular Biology 5, 471–77 (1976), R. L. Rodriquez et al, Construction and Characterization of Cloning Vehicles, in *Molecular Mechanisms in the Control of Gene Expression*, pp. 471–77, Academic Press, Inc. (1976). Plasmid pBR 322 is characterized and the manner of its derivation fully described in F. Bolivar et al, "Construction and Characterization of New Cloning Vehicles II. A Multipurpose Cloning System", *Gene* (November 1977)

B. Construction of Plasmid pBH10

Five micrograms of plasmid pBR322 DNA was digested with 10 units of the restriction endonuclease EcoRI in 100 mM Tris-HCl pH 7.6, 100 mM NaCl, 6 mM MgCl$_2$ at 37° C. for 30 min. The reaction was terminated by phenolchloroform extraction; the DNA was then precipitated with two and a half volumes of ethanol and resuspended in 50 μl of T4 DNA polymerase buffer (67 mM Tris-HCl pH 8.8, 6.7 mM MgCl$_2$, 16.6 mM (NH$_4$)$_2$SO$_4$, 167 μg/ml bovine serum albumin, 50 μM of each of the dNTP's; A. Panet et al, *Biochem.* 12, 5045 (1973). The reaction was started by the addition of 2 units of T4 DNA polymerase. After incubation for 30 min at 37° the reaction was terminated by a phenol-chloroform extraction of the DNA followed by precipitation with ethanol. Three micrograms of λ plac5 DNA (Shapiro et al *Nature* 224. 768 (1969)) was digested for 1 hr at 37° C. with the restriction enzyme HaeIII (3 units) in 6 mM Tris-HCl pH 7.6, 6 mM MgCl$_2$, 6 mM β-mercaptoethanol in a final volume of 20 μl. The reaction was stopped by heating for 10 min at 65° C. The pBR322 treated DNA was mixed with the HaeIII digested λ plac5 DNA and blunt-end ligated in a final volume of 30 μl with 1.2 units of T4 DNA ligase (hydroxylapatite fraction; A. Panet et al, supra) in 20 mM Tris-HCl pH 7.6, 10 mM MgCl$_2$, 10 mM dithiothreitol, 0.5 mM ATP for 12 hrs at 12° C. The ligated DNA mixture was dialyzed against 10 mM Tris-HCl pH 7.6, and used for transformation of *E. coli* strain RR1. Transformants were selected for tetracycline and ampicillin resistance on minimal medium, plates containing 40 µg/ml of 5-bromo-4-chloro-colylgalactoside (X-gal) medium (J. H. Miller, Experiments in Molecular Genetics (Cold Spring Harbor, N.Y., 1972)). Colonies constitutive for the synthesis of β-galactosidase were identified by their blue color. After screening 45 independently isolated blue colonies, three of them were found to contain plasmid DNA carrying two EcoRI sites separated by approximately 200 base pairs. The position of an asymmetrically located HhaI fragment in the 203 b.p. HaeIII lac control fragment (W. Gilbert et al, in Protein-Ligand Interactions, H. Sand and G. Blauer, Eds. (De Gruyter, Berlin, (1975) pp. 193–210) allows for the determination of the orientation of the HaeIII fragment, now an EcoRI fragment, in these plasmids. Plasmid pBH10 was shown to carry the fragment in the desired orientation, i.e., lac transcription going into the Tc$^r$ gene of the plasmid.

C. Construction of Plasmid pBH20

Plasmid pBH10 was next modified to eliminate the EcoRI site distal to the lac operator. This was accomplished by preferential EcoRI endonuclease cleavage at the distal site involving partial protection by RNA polymerase of the other EcoRI site localized between the Tc$^r$ and lac promoters, which are only about 40 base pairs apart. After binding RNA polymerase, the DNA (5 µg) was digested with EcoRI (1 unit) in a final volume of 10 µl for 10 min at 37° C. The reaction was stopped by heating at 65° C. for 10 min. The EcoRI cohesive termini were digested with S1 nuclease in 25 mM Na-acetate pH 4.5, 300 mM NaCl, 1 mM ZnCl$_2$ at 25° C. for 5 min. The reaction mixture was stopped by the addition of EDTA (10 mM final) and Tris-HCl pH 8 (50 mM final). The DNA was phenol-chloroform extracted, ethanol precipitated and resuspended in 100 µl of T4 DNA ligation buffer. T4 DNA ligase (1 µl) was added and the mixture incubated at 12° C. for 12 hr. The ligated DNA was transformed in *E. coli* strain RR1, and Ap$^r$Tc$^r$ transformants were selected on X-gal-antibiotic medium. Restriction enzyme analysis of DNA screened from 10 isolated blue colonies revealed that these clones carried plasmid DNA with one EcoRI site. Seven of these colonies had retained the EcoRI site located between the lac and Tc$^r$ promotors. The nucleotide sequence from the EcoRI site into the lac-control region of one of these plasmids, pBH20, was confirmed. This plasmid was next used to clone the somatostatin gene.

D. Construction of Plasmid pSOM1

Twenty micrograms of the plasmid pBH20 was digested to completion with restriction endonucleases EcoRI and BamHI in a final volume of 50 µl. Bacterial alkaline phosphatase was added (0.1 unit of Worthington BAPF) and incubation was continued for 10 min at 65° C. The reactions were terminated by phenol-chloroform extraction and the DNA was precipitated with 2 volumes of ethanol, centrifuged and dissolved in 50 µl 10 mM Tris-HCl pH 7.6, 1 mM EDTA. The alkaline phosphatase treatment effectively prevents self-ligation of the EcoRI, BamHI treated pBH20 DNA, but circular recombinant plasmids containing somatostatin DNA can still be formed upon ligation. Since *E. coli* RR1 is transformed with very low efficiency by linear plasmid DNA, the majority of the transformants will contain recombinant plasmids. Fifty microliters of somatostatin DNA (4 µg/ml) were ligated with 25 µl of the BamHI, EcoRI, alkaline phosphatase-treated pBH20 DNA in a total volume of 50 µl containing 20 mM Tris-HCl pH 7.6, 10 mM MgCl$_2$, 10 mM dithiothreitol, 0.5 mM ATP, and 4 units of T4 DNA ligase at 22° C. After 10, 20 and 30 min, additional somatostatin DNA (40 ng) was added to the reaction mixture (the gradual addition of somatostatin DNA may favor ligation to the plasmid over self-ligation). Ligation was continued for 1 hr followed by dialysis of the mixture against 10 mM Tris-HCl pH 7.6. In a control experiment, BamHI, EcoRI, alkaline phosphatase-treated pBH20 DNA was ligated in the absence of somatostatin DNA under similar conditions. Both preparations were used without further treatment to transform *E. coli* RR1. The transformation experiments were carried out in a P3 physical containment facility. (National Institutes of Health, U.S.A., Recombinant DNA Reasearch Guidelines, 1976). Transformants were selected on minimal medium plates containing 20 µg/ml Ap and 40 µg/ml X-gal. Ten transformants, which were all sensitive to Tc, were isolated. For reference these were designated pSOM1, pSOM2, etc. . . pSOM10. In the control experiment no transformants were obtained. Four out of the ten transformants contained plasmids with both an EcoRI site and BamHI site. The size of the small EcoRI, BamHI fragment of these recombinant plasmids was in all four instances similar to the size of the in vitro prepared somatostatin DNA. Base sequence analysis according to Maxam and Gilbert *Proc. Nat. Acad. Sci. U.S.A.* 74, 560 (1977), revealed that the plasmid pSOM1 had the desired somatostatin DNA fragment inserted.

The DNA sequence analysis of the clone carrying plasmid pSOM1 predicts that it should produce a peptide comprising somatostatin. However no somatostatin radioimmune activity has been detected in extracts of cell pellets or culture supernatants, nor is the presence of somatostatin detected when the growing culture is added directly to 70% formic acid and cyanogen bromide. *E. coli*. RR1 extracts have been observed to degrade exogenous somatostatin very rapidly. The absence of somatostatin activity in clones carrying plasmid pSOM1 could well result from intracellular degradation by endogenous proteolytic enzymes. Plasmid pSOM1 was accordingly employed to construct a plasmid coding for a precursor protein comprising somatostatin and sufficiently large as to be expected to resist proteolytic degradation.

E. The Construction of Plasmids pSOM11 and pSOM11-3

A plasmid was constructed in which the somatostatin gene could be located at the C-terminus of the β-galactosidase gene, keeping the translation in phase. The presence of an ECoRI site near the C-terminus of this gene and the available amino acid sequence of this protein (B. Polisky et al, *Proc. Nat. Acad. Sci. U.S.A.* 73, 3900 (1976), A. V. Fowler et al, Id. at 74, 1507 (1976), A. I. Bukhari et al, *Nature New Biology* 243, 238 (1973) and K. E. Langley, *J. Biol. Chem.* 250, 2587 (1975)) permitted insertion of the EcoRI BamHi somatostatin gene into the EcoRI site while maintaining the proper reading frame. For the construction of such a plasmid, pSOM1 DNA (50 µg) was digested with the restriction enzymes EcoRI and PstI in a final volume of 100 µl. A preparative 5% polyacrylamide gel was used to separate the large Pst-EcoRI fragment that carries the somatostatin gene from the small fragment carrying the lac control elements. The large band was excised from the gel and the DNA eluted by slicing the gel into small pieces and extracting the DNA at 65° C. overnight. In a similar way plasmid pBR322 DNA (50 µg) was digested with pstI and EcoRI restriction endonucleases and the two resulting DNA fragments purified by preparative electrophoresis on a 5% Polyacrylamide gel. The small PstI-EcoRI fragment from pBR322 (1 µg) was ligated with the large PstI-ECoRI DNA fragment (5 ug) from pSOM1 in a final volume of 50 µl with 1 unit of T4 DNA ligase at 12° C. for 12 hrs. The ligated mixture was used to transform *E. coli* RR1, and transformants were selected for ampicillin resistance on X-gal medium. As expected, almost all the Ap$^r$ transformants (95%) gave white colonies (no lac operator) on X-gal indicator plates. The resulting plasmid, pSOM11, was used in the construction of plasmid pSOM11-3. A mixture of 5 μg of pSOM11 DNA and 5 μg of λ plac$^5$ DNA was digested with EcoRI (10 units for 30 min at 37° C.). The restriction endonuclease digestion was terminated by phenol-chloroform extraction. The DNA was then ethanol-precipitated and resuspended in T4 DNA ligase buffer (50 λl). T4 DNA ligase (1 unit) was added to the mixture and incubated at 12° C. for 12 hrs. The ligated mixture was dialyzed against 10 mM Tris-HCl pH 7.6 and used to transform *E. Coli* strain RR1. Transformants were selected for Ap$^r$ on X-gal plates containing ampicillin and screened for constitutive β-galactosidase production. Approximately 2% of the colonies were blue (pSOM11-1, 11-2 etc.). Restriction enzyme analysis of plasmid DNA obtained from these clones revealed that all the plasmids carried a new EcoRI fragment of approximately 4.4 megadaltons, which carries the lac operon control sites and most of the β-galactosidase gene. Because two orientations of the EcoRI fragment are possible, the asymmetric location of a HindIII restriction site was used to determine which of these colonies were carrying this EcoRI fragment with lac transcription proceeding into the somatostatin gene. HindIII-BamHI double digestions indicated that only the clones carrying plasmids pSOM11-3, pSOM11-5, pSOM11-6 and pSOM11-7 contained the EcoRI fragment in this orientation.

4. Radioimmune Assay for Somatostatin Activity

The standard radioimmune assays (RIA) for somatostatin (A. Arimura et al, *Proc. Soc. Exp. Biol. Med.* 148, 784 (1975)) were modified by decreasing the assay volume and using phosphate buffer. Tyr$^{11}$ somatostatin was iodinated using a chloramine T procedure. (Id.) To assay for somatostatin, the sample, usually in 70% formic acid containing 5 mg/ml of cyanogen bromide was dried in a conical polypropylene tube (0.7 ml, Sarstedt) over moist KOH under vacuum. Twenty microliters of PBSA buffer (75 mM NaCl; 75 mM sodium phosphate, pH 7.2; 1 mg/ml bovine serum albumin; and 0.2 mg/ml sodium azide) was added, followed by 40 μl of a [$^{125}$I] somatostatin "cocktail" and 20 μl of a 1,000-fold dilution in PBSA of rabbit antisomatostatin immune serum S39 (Vale et al, *Metabolism* 25, 1491 (1976). The [$^{125}$I] somatostatin cocktail contained per ml of PBSA buffer: 250 μg normal rabbit gamma globulin (Antibodies, Inc.), 1500 units protease inhibitor ("Trasylol", Calbiochem) and about 100,000 counts of [$^{125}$I] Tyr$^{11}$-somatostatin. After at least 16 hour at room temperature, 0.333 ml of goat anti-rabbit gamma globulin (Antibodies, Inc., P=0.03) in PBSA buffer was added to the sample tubes. The mixture was incubated 2 hr at 37° C., cooled to 5° C., then centrifuged at 10,000×g for 5 min. The supernatant was removed and the pellet counted in a gamma counter. With the amount of antiserum used, 20% of the counts was precipitated with no unlabeled competing somatostatin. The background with infinite somatostatin (200 ng) was usually 3%. One-half maximum competition was obtained with 10 pg of somatostatin. Initial experiments with extracts of *E. Coli* strain RR1 (the recipient strain) indicated that less than 10 pg of somatostatin could easily be detected in the presence of 16 μg or more of cyanogen bromide-treated bacterial protein. More than 2 μg of protein from formic acid-treated bacterial extracts interfered somewhat by increasing the background, but cyanogen bromide cleavage greatly reduced this interference. Reconstruction experiments showed that somatotatin is stable in cyanogen bromide-treated extracts.

A. Competition by Bacterial Extracts

Strains *E. Coli* RR1 (pSOM11-5) and *E. Coli* RR1 (pSOM11-4) were grown at 37° C. to 5×10$^8$ cells/ml in Luria broth. Then IPTG was added to 1 mM and growth continued for 2 hr. One-milliliter aliquots were centrifuged for a few seconds in an Eppendorf centrifuge and the pellets were suspended in 500 μl of 70% formic acid containing 5 mg/ml cyanogen bromide. After approximately 24 hr at room temperature, aliquots were diluted tenfold in water and the volumes indicated in FIG. 6 were assayed in triplicate for somatostatin. In FIG. 6 "B/B$_o$" is the ratio of [$^{125}$I] somatostatin bound in the presence of sample to that bound in the absence of competing somatostatin. Each point is the average of triplicate tubes. The protein content of the undiluted samples was determined to be 2.2 mg/ml for *E. Coli* RR1 (pSOM11-5) and 1.5 mg/ml for *E. Coli* RR1 (pSOM-4).

B. The Initial Screening of pSOM11 Clones for Somatostatin

Cyanogen bromide-treated extracts of 11 clones (pSOM11-2, pSOM11-3, etc.) were made as described above for the case of FIG. 6. Thirty microliters of each extract was taken in triplicate for radioimmune assay, whose results appear from FIG. 7. The range of assay points is indicated. The values for picograms somatostatin were read from a standard curve obtained as part of the same experiment.

The radioimmune assay results described thus far may be summarized as follows. In contrast to the results of experiments with pSOM1, four clones (pSOM11-3 11-5, 11-6, and 11-7) were found to have easily detectable somatostatin radioimmune activity FIGS. 6 and 7. Restriction fragment analysis revealed that pSOM11-3, pSOM11-5, pSOM11-6 and pSOM111-7 had the desired orientation of the lac operon, whereas pSOM11-2 and 11-4 had the opposite orientation. Thus there is a perfect correlation between the correct orientation of the lac operon and the production of somatostatin radioimmune activity.

C. Effects of IPTG Induction and CNBr Cleavage on Positive and Negative Clones

The design of the somatostatin plasmid predicts that the synthesis of somatostatin would be under the control of the lac operon. The lac repressor gene is not included in the plasmid and the recipient strain (*E. Coli* RR1) contains the wild type chromosomal lac repressor gene which produces only 10 to 20 repressor molecules per cell. The plasmid copy number (and therefore the number of lac operators) is approximately 20–30 per cell, so complete repression is impossible. As shown in Table III, infra the specific activity of somatostatin in *E. coli* RR1 (pSOM11-3) was increased by IPTG, an inducer of the lac operon. As expected, the level of induction was low, varying from 2.4 to 7 fold. In experiment 7 (Table III) α activity, a measure of the first 92 amino acids of β-galactosidase, also was induced by a factor of two. In several experiments no detectable somatostatin radioimmune activity can be detected prior to cyanogen bromide cleavage of the total cellular protein. Since the antiserum used in the radioimmune assay, S 39, requires a free N-terminal alanine, no activity was expected prior to cyanogen bromide cleavage.

TABLE III

Somatostatin Radioimmune Specific Activity
Abbreviations: Luria Broth, LB; isopropylthiogalactoside,
IPTG; cyanogen bromide, CNBr; somatostatin, SS.
Protein was measured by the method of Bradford, Anal.
Biochem. 72, 248 (1976).

| Experiment Number | Strain | Medium | IPTG 1 mM | CNBr 5 mg/ml | pg SS/ug protein |
|---|---|---|---|---|---|
| 1 | 11-2 | LB | + | + | <0.1 |
|   | 11-3 | LB | + | + | 12 |
|   | 11-4 | LB | + | + | <0.4 |
|   | 11-5 | LB | + | + | 15 |
| 2 | 11-3 | LB | + | + | 12 |
|   | 11-3 | LB | + | − | <0.1 |
| 3 | 11-3 | LB | + | + | 61 |
|   | 11-3 | LB | − | + | <8 |
|   | 11-3 | LB | + | − | <0.1 |
| 4 | 11-3 | LB | + | + | 71 |
|   | 11-3 | VB + glycerol* | + | + | 62 |
| 5 | 11-3 | LB + glycerol | + | + | 250 |
| 6 | 11-3 | LB | + | + | 320 |
|   | 11-2 | LB | + | + | <0.1 |
| 7 | 11-3 | LB | + | + | 24 |
|   | 11-3 | LB | − | + | 10 |

*Vogel-Bonner minimal medium plus glycerol.

D. Gel Filtration of Cyanogen Bromide—Treated Extracts

Formic acid and cyanogen-treated extracts of the positive clones (pSOM 11-3, 11-5, 11-6, and 11-7) were pooled (Total volume 250 μl), dried, and resuspended in 0.1 ml of 50% acetic acid. [$^3$H] leucine was added and the sample was applied to an 0.7×47 cm column of Sephadex G-50 in 50% acetic acid. Fifty-microliter aliquots of the column fractions were assayed for somatostatin. Pooled negative clone extracts (11-2, 11-4, and 11—11) were treated identically. The results appear from FIG. 5C. On the same column known somatostatin (Beckman Corp.) elutes as indicated (SS). In this system, somatostatin is well-separated from excluded large peptides and fully included small molecules. Only extracts of clones positive for somatostatin exhibited radioimmune activity in the column fractions and this activity elutes in the same position as chemically synthesized somatostatin.

SUMMARY OF ACTIVITY INFORMATION

The data establishing the synthesis of a polypeptide containing the somatostatin amino acid sequence are summarized as follows: (1) Somatostatin radioimmune activity is present in E. coli cells having the plasmid pSOM11-3, which contains a somatostatin gene of proven correct sequence and has the correct orientation of the lac EcoRI DNA fragment. Cells with the related plasmid pSOM11-2, which has/the same somatostatin gene but an opposite orientation of the lac EcoRI fragment, produce no detectable somatostatin activity; (2) As predicted by the design scheme, no detectable somatostatin radioimmune activity is observed until after cyanogen bromide treatment of the cell extract; (3) The somatostatin activity is under control of the lac operon as evidenced by induction by IPTG, an inducer of the lac operon; (4) The somatostatin activity co-chromatographs with known somatostatin on Sephadex G-50; (5) The DNA sequence of the cloned somatostatin gene is correct. If translation is out of phase, a peptide will be made which is different from somatostatin at every position. Radioimmune activity is detected indicating that a peptide closely related to somatostatin is made, and translation must be in phase. Since translation occurs in phase, the genetic code dictates that a peptide with the exact sequence of somatostatin is made; (6) Finally, the above samples of E. coli RR1 (pSOM11-3) extract inhibit the release of growth hormone from rat pituitary cells, whereas samples of E. coli RR1 (pSOM11-2) prepared in parallel and with identical protein concentration have no effect on growth hormone release.

STABILITY, YIELD, AND PURIFICATION OF SOMATOSTATIN

The strains carrying the EcoRI lac operon fragment (pSOM11-2, pSOM11-3, etc.) segregate with respect to the plasmid phenotype. For example, after about 15 generations, about one-half of the E. Coli RR1 (pSOM11-3) culture was constitutive for β-galactosidase, i.e., carried the lac operator, and of these about half were ampicillin resistant. Strains positive (pSOM11-3) and negative (pSOM11-2) for somatostatin are unstable, and therefore, the growth disadvantage presumably comes from the overproduction of the large but incomplete and inactive galactosidase. The yield of somatostatin has varied from 0,001 to 0.03% of the total cellular protein (Table 1) probably as the result of the selection for cells in culture having plasmids with a deleted lac region. The highest yields of somatostatin have been from preparations where growth was started from a single ampicillin resistant, constitutive colony. Even in these cases, 30% of the cells at harvest had deletions of the lac region, Storage in the frozen state (lyophilization) and growth to harvest from a single such colony is accordingly indicated for the system described. Yields may be increased by, e.g., resort to bacterial strains which overproduce lac repressor such that expression of precursor protein is essentially totally repressed prior to induction and harvest. Alternatively, as previously discussed, a tryptophan or other operator-promoter system which ordinarily is totally repressed may be employed.

In the crude extract resulting from cell disruption in, e.g., an Eaton Press, the β-galactosidase-somatostatin precursor protein is insoluble and is found in the first low speed centrifugation pellet. The activity can be solubilized in 70% formic acid, 6M guanididium hydrochloride, or 2% sodium dodecyl sulfate. Most preferably, however, the crude extract from the Eaton Press is extracted with 8M urea and the residue cleaved with cyanogen bromide. In initial experiment somatostatin activity derived from E. coli. strain RR1 (pSOM11-3) has been enriched approximately 100-fold by alcohol extraction of the cleavage product and chromatography on Sephadex G-50 in 50% acetic acid. When the product is again chromatographed on Sephadex G-50 and then subjected to high pressure liquid chromatography, substantially pure somatostatin may be obtained.

II. HUMAN INSULIN

The techniques previously described were next applied to the production of human insulin. Thus, the genes for insulin B chain (104 base pairs) and for insulin A chain (77 base pairs) were designed from the amino acid sequence of the human polypeptides, each with single-stranded cohesive termini for the EcoRI and BaMHI restriction endonucleases and each designed for insertion separately into pBR322 plasmids. The synthetic fragments, deca- to pentadeca-nucleotides, were synthesized by the block phosphotriester method using trinucleotides as building blocks and ultimately purified with high performance liquid chromatography (HPLC). The human insulin A and B Chain synthetic genes were then cloned separately in plasmid pBR322. The cloned synthetic genes were fused to an *E. Coli* β-galactosidase gene as before to provide efficient transcription, translation, and a stable precursor protein. Insulin peptides were cleaved from β-galactasidase precursor, detected by radioimmunoassy, and purified. Insulin radioimmunoassay activity was then generated by mixing the *E. Coli* products.

1. Design and Synthesis of Human Insulin Genes

The genes constructed for human insulin are depicted in FIG. 9. The genes for human insulin, B chain and A chain, were designed from the amino acid sequences of the human polypeptides. The 5' ends of each gene have single stranded cohesive termini for the EcoRI and BamHI restriction endonucleases, for the correct insertion of each gene into plasmid pBR322. A HindIII endonuclease recognition site was incorporated into the middle of the B chain gene for the amino acid sequence Glu-Ala to allow amplification and verification of each half of the gene separately before the construction of the whole B chain gene. The B chain and the A chain genes were designed to be built from 29 different oligodeoxyribonucleotides, varying from decamer to pentadecamers. Each arrow indicates the fragment synthesized by the improved phosphotriester method, H1 to H8 and B1 to B12 for the B chain gene and A1 to A11 for the A chain gene.

2. Chemical Synthesis of Oligodeoxyribonucleotides

Materials and methods for synthesis of oligodeoxyribonucleotides were essentially those described in Itakura, K. et al (1975) *J. Biol. Chem.* 250, 4592 and Itakura, K. et al (1975) *J. Amer. Chem.* Soc. 97, 7327 except for these modifications:

a) The fully protected mononucleotides, 5'-O-dimethoxytrityl-3'-p-chlorophenyl-β-cyanoethyl phosphates, were synthesized from the nucleoside derivatives using the monofunctional phosphorylating agent p-chloro-phenyl-β-cyanoethyl phosphorochloridate (1.5 molar equivalent) in acetonitrile in the presence of 1-methyl imidazole Van Boom, J. B. et al (1975) *Tetrahedron* 31, 2953. The products were isolated in large scale (100 to 300 g) by preparative liquid chromatography (Prep 500 LC, Waters Associates).

b) By using the solvent extraction method [Hirose, T. et al (1978) *Tetrahedron Letters*, 2449] 32 bifunctional trimers were synthesized (see Table IV) in 5 to 10 mmole scale, and 13 trimers, 3 tetramers, and 4 dimers as the 3' terminus blocks, in 1 mmole scale. The homogeneity of the fully protected trimers was checked by thin layer chromatography on silica gel in two methanol/chloroform solvent systems: solvent a, 5% v/v and solvent b, 10% v/v (See Table IV). Starting from this library of compounds, 29 oligodeoxyribonucleotides of defined sequence were synthesized, 18 for the B chain and 11 for the A chain gene.

The basic units used to construct polynucleotides were two types of trimer block, i.e. the bifunctional trimer blocks of Table IV and corresponding 3'-terminus trimers protected by an anisoyl group at 3'-hydroxy. The bifunctional trimer was hydrolyzed to the corresponding 3'-phosphodiester component with a mixture of pyridine-triethylamine-water (3:1:1 v/v) and also to the corresponding 5'-hydroxyl component with 2% benzenesulfonic acid. The 3'-terminus block previously referred to was treated with 2% benzenesulfonic acid to give the corresponding 5'-hydroxyl. The coupling reaction of an excess of the 3-phosphodiester trimer (1.5 molar equivalent) with the 5'-hydroxyl component, however obtained, (1 molar equivalent) in the presence of 2,4,6-triisopropylbenzenesulfonyl tetrazolide (TPSTe, 3 to 4 equivalents) went almost to completion. To remove the excess of the 3' phosphodiester. reactant the reaction mixture was passed through a short silica gel column set up on a sintered glass filter. The column was washed, first with $CHCl_3$ to elute some side products and the coupling reagent, and then with $CHCl_3$:MeOH (95:5 v/v) in which almost all of the fully protected oligomer was eluted. Under these conditions, the charged 3'-phosphodiester block reactant remained in the column. Similarly, block couplings were repeated until the desired length was constructed.

TABLE IV

SYNTHESIS OF TRIMER BUILDING BLOCKS

| No | Compound* | Yield** (%) | Rf a. | Rf b. | Purity*** (%) | In FIG. 9, Present In: |
|---|---|---|---|---|---|---|
| 1. | AAG | 47 | 0.15 | 0.40 | 93 | B5, B6 |
| 2. | AAT | 49 | 0.25 | 0.52 | 95 | H1, A1, A6 |
| 3. | AAC | 52 | 0.28 | 0.55 | 93 | H5, B6, A2, A8 |
| 4. | ACT | 43 | 0.27 | 0.53 | 91 | B4, B5, A6 |
| 5. | ACC | 56 | 0.33 | 0.60 | 96 | B7 |
| 6. | ACG | 39 | 0.18 | 0.45 | 90 | H5, B7 |
| 7. | AGG | 45 | 0.10 | 0.26 | 89 | H6, H7, B9 |
| 8. | AGT | 33 | 0.14 | 0.40 | 96 | B9, A2, A11 |
| 9. | AGC | 50 | 0.19 | 0.48 | 92 | H8, B1, A5, A10 |
| 10. | AGA | 48 | 0.24 | 0.50 | 91 | A9, |
| 11. | TTC | 44 | 0.26 | 0.52 | 95 | B4, B7, A3 |
| 12. | TTC | 49 | 0.11 | 0.31 | 94 | H3, H5, A2, A3, A5 |
| 13. | TCT | 58 | 0.24 | 0.49 | 96 | A4 |
| 14. | TCA | 45 | 0.28 | 0.53 | 92 | H1, H2, H4, A1 |
| 15. | TCG | 39 | 0.12 | 0.34 | 91 | A2 |
| 16. | TGG | 32 | 0.10 | 0.28 | 87 | H3, A1, A10 |
| 17. | TGC | 51 | 0.18 | 0.47 | 93 | H6, B2, A4, A7, A8 |
| 18. | TGA | 46 | 0.12 | 0.37 | 94 | H7 |
| 19. | TAC | 61 | 0.22 | 0.50 | 90 | B4, A11 |
| 20. | TAA | 55 | 0.17 | 0.44 | 95 | B5, A10 |
| 21. | CCT | 53 | 0.30 | 0.55 | 97 | H3, H4, B10 |
| 22. | CAC | 47 | 0.25 | 0.51 | 92 | A3 |
| 23. | CAA | 58 | 0.25 | 0.51 | 93 | H2, H6, H8, A7 |
| 24. | CTT | 41 | 0.28 | 0.54 | 92 | B2, B9, A4 |
| 25. | CGA | 40 | 0.27 | 0.52 | 93 | A7 |

TABLE IV-continued

SYNTHESIS OF TRIMER BUILDING BLOCKS

| No | Compound* | Yield** (%) | Rf a. | Rf b. | Purity*** (%) | In FIG. 9, Present In: |
|----|-----------|-------------|-------|-------|---------------|------------------------|
| 26. | CGT | 75 | 0.25 | 0.50 | 89 | H2, H4, B3, B1 |
| 27. | GGT | 35 | 0.09 | 0.26 | 90 | B3 |
| 28. | GTT | 46 | 0.18 | 0.45 | 93 | B2 |
| 29. | GTA | 38 | 0.25 | 0.50 | 95 | B6, B8, A6 |
| 30. | GAA | 39 | 0.15 | 0.39 | 88 | B7, B3, B8, A5 |
| 31. | GAT | 52 | 0.22 | 0.49 | 89 | B10, A9 |
| 32. | GCA | 42 | 0.14 | 0.39 | 93 | A9 |

*Fully protected trideoxynucleotides; 5-0-Dimethoxytrityl-3'-p-Chlorophenyl-β-cyanoethyl phosphate.
**Yield was the overall yield calculated from the 5'-hydroxylmonomers.
***Based on HPLC analysis.

High performance liquid chromatography (BPLC) was used extensively during oligonucleotide synthesis for a) analysis of each trimer and tetramer block, b) analysis of the intermediate fragments (hexamers, monomers, and decamers), c) analysis of the last coupling reaction, and d) purification of the final products. The HPLC was performed by using a Spectra-Physics 3500B liquid chromatograph. After removal of all protecting groups by conc. NH$_4$OH at 50° C. (6 h) and 80% AcOH at room temperature (15 min), the compounds were analyzed on a Permaphase AAX (DuPont) [Van Boom, J. et al (1977) J. Chromatography 131, 169.] column (1 mX 2 mm), using a linear gradient of solvent B (0.05M KH$_2$PO$_4$, −1.0M KCl, ph 4.5) in solvent A (0.01M KH$_2$PO$_4$, pH 4.5). The gradient was formed starting with buffer A and applying 3% of buffer B per minute. The elution was performed at 60° C., with a flow rate of 2 ml per minute. The purification of the 29 final oligonucleotides also was performed on Permaphase AAX, under the same conditions reported above. The desired peak was pooled, desalted by dialysis, and lyophilized. After labeling the 5' termini with (γ-$^{32}$P)ATP using T$_4$ polynucleotide kinase, the homogeneity of each oligonucleotide was checked by electrophoresis on a 20% polyacrylamide gel.

3. Assembly and Cloning of B Chain Gene and the A Chain Gene

The gene for the B chain of insulin was designed to have an EcoRI restriction site on the left end, a HindIII site in the middle and BamHI site at the right end. This was done so that both halves, the left EcoRI-HindIII half (BH) and the right HindIII-BamHI half (BB), could be separately cloned in the convenient cloning vehicle pBR322 and after their sequences had been verified, joined to give the complete B gene (FIG. 10). The BB half was assembled by ligation from 10 oligodeoxyribonucleotides, labeled B1 to B10 in FIG. 9, made by phosphotriester chemical synthesis. B1 and B10 were not phosphorylated, thereby eliminating unwanted polymerization of these fragments through their cohesive ends (HindIII and BamHI). After purification by preparative acrylamide gel electrophoresis and elution of the largest DNA band, the BB fragment was inserted into plasmid pBR322 which had been cleaved with HindIII and BamHI. About 50% of the ampicillin resistant colonies derived from the DNA were sensitive to tetracycline, indicating that a nonplasmid HindIII-BamHI fragment had been inserted. The small HindIII-BamHI fragments from four of these colonies (pBB101 to pBB104) were sequenced and found to be correct as designed.

The BH fragment was prepared in a similar manner and inserted into pBR322 which had been cleaved with EcoRI and HindIII restriction endonucleases. Plasmids from three ampicillin resistant, tetracycline sensitive transformants (pBH1 to pBH3) were analyzed. The small EcoRI-HindIII fragments were found to have the expected nucleotide sequence.

The A chain gene was assembled in three parts. The left four, middle four, and right four oligonucleotides (see FIG. 9) were ligated separately, then mixed and ligated (oligonucleotides A1 and A12 were unphosphorylated). The assembled A chain gene was phosphorylated, purified by gel electrophoresis, and cloned in pBR322 at the ECoRI-BamHI sites. The ECoRI-BamHI fragments from two ampicillin resistant, tetracycline sensitive clones (pA10, pa11) contained the desired A gene sequence.

4. Construction of Plasmids for Expression of A and B Insulin Genes

FIG. 10 illustrates the construction of the lacinsulin B plasmid (pIB1). Plasmids pBH1 and pBB101 were digested with EcoRI and HindIII endonucleases. The small B fragment of pBH1 and the large fragment of pBB101 (containing the BB fragment and most of pBR322) were purified by gel electrophoresis, mixed, and ligated in the presence of EcoRI-cleaved λ plac5. The megadalton EcoRI fragment of λ plac5 contains the lac control region and the majority of the β-galactosidase structural gene. The configuration of the restriction sites ensures correct joining of BE to BB. The lac EcoRI fragment can insert in two orientations thus, only half of the clones obtained after transformation should have the desired orientation. The orientation of ten ampicillin resistant, β-galactosidase constitutive clones were checked by restriction analysis. Five of these colonies contained the entire B gene sequence and the correct reading frame from the β-galactosidase gene into the B chain gene. One, pIB1, was chosen for subsequent experiments.

In a similar experiment, the 4.4 megadalton lac fragment from λ plac5 was introduced into the pA11 plasmid at the EcoRI site to give pIA1. pIA1 is identical to pIB1 except that the A gene fragment is substituted for the B gene fragment. DNA sequence analysis demonstrated that the correct A and B chain gene sequences were retained in pIA1 and pIB1 respectively.

5. Expression

The strains which contain the insulin genes correctly attached to β-galactosidase both produce large quantities of a protein the size of β-galactosidase. Approximately 20% of the total cellular protein was this β-galactosidase-insulin A or B chain hybrid. The hybrid proteins are insoluble and were found in the first low speed pellet where they constitute about 50% of the protein.

To detect the expression of the insulin A and B chains, we used a radioimmunoassay (RIA) based on the reconstitution of complete insulin from the separate chains. The insulin reconstitution procedure of Katsoyannis et al (1967) *Biochemistry* 6, 2642–2655, adapted to a 27-microliter assay volume, provides a very suitable assay. Easily detectable insulin activity is obtained after mixing and reconstituting S-Sulfonated derivatives of the insulin chains. The separate S-sulfonated chains of insulin do not react significantly, after reduction and oxidation, with the anti-insulin antibody used.

To use the reconstitution assay we partially purified the β-galactosidase-A or B chain hybrid protein, cleaved with cyanogen bromide, and formed S-sulfonated derivatives.

The evidence that we have obtained correct expression from chemically synthesized genes for human insulin can be summarized as follows: a) Radioimmune activity has been detected for both chains. b) The DNA sequences obtained after cloning and plasmid construction have been directly verified to be correct as designed. Since radioimmune activity is obtained, translation must be in phase. Therefore, the genetic code dictates that peptides with the sequences of human insulin are being produced. c) The *E. Coli* products, after cyanogen bromide cleavage, behave as insulin chains in three different chromatographic systems which separate on different principles (gel filtration, ion exchange, and reversed phase RPLC). d) The *E coli* produced A chain has been purified on a small scale by HPLC and has the correct amino acid composition.

We claim:

1. A process for the production of a polypeptide comprising a preselected functional mammalian polypeptide or polypeptide intermediate therefor in a microbial cell culture, said process comprising effecting expression of said polypeptide in a microorganism transformed with a replicable cloning vehicle comprising DNA encoding said polypeptide which DNA is under the operative control of an expression control region functional in *E. coli* comprising operatively linked promoter, operator and ribosome binding site DNA.

2. The process of claim 1 wherein said expression control region DNA is derived from the lactose operon, lambda promoter operator, arabinose operon, colicine E1, galactose, alkaline phosphatase, or tryptophan operon.

* * * * *

UNITED STATES PATENT AND TRADEMARK OFFICE
CERTIFICATE OF CORRECTION

PATENT NO. : 5,583,013

DATED : December 10, 1996

INVENTOR(S) : Itakura et al.

It is certified that error appears in the above-indentified patent and that said Letters Patent is hereby corrected as shown below:

Column 2, line 38 delete " [new paragraph] Plac" and insert therefor --plac--.

Column 3, line 17 delete "Hershfel" and insert therefor --Hershfield--.

Column 4, line 1 delete ""cDNA")" and insert therefor --"cDNA")--.

Column 4, line 4 delete "Which" and insert therefor --which--.

Column 5, line 1 delete "epicillin" and insert therefor --ampicillin--.

Column 5, line 64 delete "(1976)" and insert therefor --(1996))--.

Column 6, line 27 delete "set" and insert therefor --ser--.

Column 6, line 61 delete "mutandts" and insert therefor --mutandis--

Column 7, line 6 delete "DNA" and insert therefor --cDNA--.

Column 7, line 6 delete "mRNA" and insert therefor --mRNA--.

Column 8, line 17 delete "vital" and insert therefor --viral--.

Column 8, line 45 delete "data" and insert therefor --dara--.

UNITED STATES PATENT AND TRADEMARK OFFICE
CERTIFICATE OF CORRECTION

PATENT NO. : 5,583,013
DATED : December 10, 1996
INVENTOR(S) : Itakura et al.

It is certified that error appears in the above-indentified patent and that said Letters Patent is hereby corrected as shown below:

Column 10, line 12 delete "$^{-M}_{\ B}$" and insert therefor --$^-M_B$--.

Column 10, line 24 delete "$^{hsr-,hsm}_{\ \ \ \ \ \ \ \ k}{}^+$" and insert therefor --hsr,$^-$hsm$_k{}^+$--.

Column 10, line 54 delete "rain" and insert therefor --min--.

Column 11, line 34 delete "(1977)" and insert therefor --(1997))--.

Column 12, line 36 delete "(1976)" and insert therefor --(1976))--.

Column 14, line 50 delete "BamHi" and insert therefor --BamHI--.

Column 14, line 65 delete "ug" and insert therefor --$\mu$g--.

Column 14, line 65 delete " PstI-ECoRI" and insert therefor --EcoRi--.

Column 15, line 11 delete "$\lambda$1" and insert therefor --$\mu$1--.

Column 15, line 44 delete "(1976)" and insert therefor --(1976))--.

Column 15, line 49 delete "16 hour" and insert therefor --16 hours--.

UNITED STATES PATENT AND TRADEMARK OFFICE
CERTIFICATE OF CORRECTION

PATENT NO. : 5,583,013

DATED : December 10, 1996

INVENTOR(S) : Itakura et al.

It is certified that error appears in the above-indentified patent and that said Letters Patent is hereby corrected as shown below:

Column 17, line 36 delete "11—11" and insert therefor --11-11--.

Column 17, line 55 delete "has/the" and insert therefor --has the--.

Column 19, line 34 delete "nucleoside" and insert therefor --nucleotide--.

Column 20, line 30 delete "phosphodiester. reactant" and insert therefor --phosphodiester reactant--.

Column 21, line 24 delete "[new paragraph]".

Column 22, line 44 delete "BE" and insert therefor --BH--.

Column 24, line 3 delete "RPLC)" and insert therefor --HPLC)--.

Signed and Sealed this

Second Day of December,1997

*Attest:*

BRUCE LEHMAN

*Attesting Officer*     *Commissioner of Patents and Trademarks*